United States Patent
Roder et al.

(12)

(10) Patent No.: US 7,534,587 B2
(45) Date of Patent: *May 19, 2009

(54) **MICROSATELLITE MARKERS FOR PLANTS OF THE GENUS *TRITICEAE* AND USE THEREOF**

(76) Inventors: Marion Roder, Reuthestrasse 9, D-06507 Rieder (DE); Jens Plaschke, A.-Mücke-Ring 12B, D-01662 Meissen (DE); Martin Ganal, Reuthestrasse 9, D-06507 Rieder (DE)

( * ) Notice: Subject to any disclaimer, the term of this patent is extended or adjusted under 35 U.S.C. 154(b) by 698 days.

This patent is subject to a terminal disclaimer.

(21) Appl. No.: 10/697,527

(22) Filed: Oct. 30, 2003

(65) Prior Publication Data
US 2004/0146898 A1    Jul. 29, 2004

Related U.S. Application Data

(62) Division of application No. 08/983,605, filed on May 1, 1998, now Pat. No. 6,720,137.

(51) Int. Cl.
*C12P 19/34* (2006.01)
*C12Q 1/68* (2006.01)
*C07H 21/04* (2006.01)

(52) U.S. Cl. .......................... 435/91.1; 435/91.2; 435/6; 536/23.1; 536/24.3

(58) Field of Classification Search .................. None
See application file for complete search history.

(56) References Cited

OTHER PUBLICATIONS

Roder et al. Mol. Gen. Genet (1995) 246:327-333.*
Devos et al. Theor Appl. Genet. (1995) 90:247-252.*

* cited by examiner

*Primary Examiner*—Juliet C Switzer
(74) *Attorney, Agent, or Firm*—Norris McLaughlin & Marcus, P.A.

(57) ABSTRACT

The invention relates to novel microsatellite markers for wheats (*Triticum aestivum*) and closely related species (Genus *Triticeae*) and to the use of said markers for the genetic analysis of plants of the *Triticum aestivum* species.

3 Claims, No Drawings

MICROSATELLITE MARKERS FOR PLANTS OF THE GENUS *TRITICEAE* AND USE THEREOF

This application is a divisional of U.S. Ser. No. 08/983,605, filed on 1 May 1998, now U.S. Pat. No. 6,720,137.

The invention relates to novel genetic, markers for wheats (*Triticum aestivum* L.) and closely related species (*Tribus Triticeae*) and to the use of said markers.

The most widely spread, known, DNA-based genetic markers are the so-called restriction, fragment length polymorphisms (RFLP) markers., For using these markers, genomic DNA is digested with restriction enzymes, separated on agarose gels and transferred to nylon membranes (Southern Blot). Specific fragments are detected by hybridization with radioactively labeled DNA probes. When mutations occur in the region of the restriction enzymes used or when smaller deletions/insertions occur, polymorphisms between different lines are found, which are passed on stably and mostly codominantly. The use of RFLP markers in hexaploid cultivated wheat is possible only to a limited extent, since only very little polymorphism is detected in wheat in this manner.

It has already been described that microsatellite markers detect significantly more polymorphism between different wheat lines than do RFLP markers. This can be attributed particularly to the occurrence of multiple alleles per locus (Röder et al., Mol. Gen. Genet. (1995) 246, 327-333). Moreover, it is known that microsatellite markers have the advantage that they can be detected by way of PCR and that therefore large amounts of samples can be analyzed more easily.

It is an object of the invention to provide novel microsatellite markers for the genetic analysis of plants of the *Triticum aestivum* species, which markers are distinguished by a degree of DNA polymorphism, which is higher than that of other molecular probes, that have been developed previously for the wheat genome.

This objective is accomplished by claims 1 to 10. The inventive markers are based on the amplification of certain hypervariable genome sections, the so-called microsatellites, with the help of their polymerase chain reaction (PCR). For specific amplification, two primers, in each to the case left and the right in the flanking sequences, are required for each microsatellite locus. On the average, these primers are 20±3 bases long and are defined by their sequences. In principle, a microsatellite marker is a sequence tagged site (STS), which is defined by two specific primers. These primers flank, in each case to the left and the right, a so-called microsatellite sequence. A microsatellite sequence is defined as a tandem repetitive repetition of a di-, tri- or tetranucleotide sequence, for example $(GA)_n$, in which $n \geq 10$. Composite microsatellite sequences also occur, such as $(GT)_n(AT)_n$, as well as imperfect sequences, in which individual bases are mutated, such as $(GA)_n CA (GA)_n$. Among various lines and varieties, there is variation in the number of repeats at a certain locus. After amplification of the microsatellites, this leads, by means of the specific primers in the flanking sequences, to PCR products of different length and, with that, to polymorphisms. These polymorphisms are passed on stably and can therefore be used as genetic markers. In some cases, null alleles (no visible fragment) also occur, when there are mutations within the binding site for the primers.

The separation and detection of the PCR products obtained can be carried out with different technical variants. For separating the fragments, highly resolving agarose gels, native polyacrylamide gels or denaturing polyacrylamide gels (=sequencing gels) can be used. Depending on the separation system, fragments are detected using ethidium bromide staining, silver staining or, after labeling the PCR fragments radioactively, using autoradiography. A further, very effective variation for separation and detection consists of the use of an automatic sequencer with dye- or fluorescence-labeled primers. For this purpose, it is necessary to synthesize a dye- or fluorescence-labeled primer from each microsatellite primer pair. PCR amplification results in a labeled product, which can be detected by the sequencing equipment. At the same time, dye- or fluorescence-labeled size standards are also separated for each sample in the same track. After that, special software enable the absolute size of each fragment, which has been separated, to be calculated and, with that, also permits fragments from different gel runs to be compared. With this method, several hundred samples can be analyzed largely automatically in a day.

Pursuant to the invention, microsatellite markers are made available, which contain the following primer pairs with assigned microsatellite sequences or a number thereof and amplify the loci of all chromosomes of the wheat genome and therefore find use for gene marking.

| WMS Number | WMS Primer Left | | WMS Primer Right | | Length (bp) in "cs" | Repeat Type | Annealing Temperature |
|---|---|---|---|---|---|---|---|
| WMS052 | 5' CTA TGA GGC GGA GGT TGA AG 3' | (SEQ. ID NO. 1) | 5' TGC GGT GCT CTT CCA TTT 3' | (SEQ. ID NO. 2) | 150 | GTimp | 60° C. |
| WMS055 | 5' GCA TCT GGT ACA CTA GCT GCC 3' | (SEQ. ID NO. 3) | 5' TCA TGG ATG CAT CAC ATC CT 3' | (SEQ. ID NO. 4) | 127 | CTimp | 60° C. |
| WMS057 | 5' TCG ATT CTG AAA GGT TCA TCG 3' | (SEQ. ID NO. 5) | 5' CGA TCA AGT AGT TGA AAG CGC 3' | (SEQ. ID NO. 6) | 224 | AAAAAimp | 60° C. |
| WMS058 | 5' TCT GAT CCC GTG AGT GTA ACA 3' | (SEQ. ID NO. 7) | 5' GAA AAA AAT TGC ATA TGA GCC C 3' | (SEQ. ID NO. 8) | 118 | CA | 60° C. |
| WMS060 | 5' TGT CCT ACA CGG ACC ACG T 3' | (SEQ. ID NO. 9) | 5' GCA TTG ACA GAT GCA CAC G 3' | (SEQ. ID NO. 10) | 211 | CA | 60° C. |
| WMS063 | 5' TCG ACC TGA TCG CCC CTA 3' | (SEQ. ID NO. 11) | 5' CGC CCT GGG TGA TGA ATA GT 3' | (SEQ. ID NO. 12) | 271 | GAA, CA, TA | 60° C. |
| WMS067 | 5' ACC ACA CAA ACA AGG TAA GCG 3' | (SEQ. ID NO. 13) | 5' CAA CCC TCT TAA TTT TGT TGG G 3' | (SEQ. ID NO. 14) | 85 | CA | 60° C. |
| WMS068 | 5' AGG CCA GAA TCT GGG AAT G 3' | (SEQ. ID NO. 15) | 5' CTC CCT AGA TGG GAG AAG GG 3' | (SEQ. ID NO. 16) | 182 | GA | 60° C. |
| WMS070 | 5' AGT GGC TGG GAG AGT GTC AT 3' | (SEQ. ID NO. 17) | 5' GCC CAT TAC CGA GGA CAC 3' | (SEQ. ID NO. 18) | 194 | GT | 60° C. |
| WMS071 | 5' GGC AGA GCA GCG ACA CTC 3' | (SEQ. ID NO. 19) | 5' CAA GTG GAG CAT TAG GTA CAC G 3' | (SEQ. ID NO. 20) | 128 | GT | 60° C. |
| WMS077 | 5' ACA AAG GTA AGC AGC ACC TG 3' | (SEQ. ID NO. 21) | 5' ACC CTG CCC GTG TTG 3' | (SEQ. ID NO. 22) | 153 | CA, GA | 55° C. |
| WMS082 | 5' ACG TTA GAA GGT GCA ATG GG 3' | (SEQ. ID NO. 23) | 5' AGT GGA TGC ACC GAC TTT G 3' | (SEQ. ID NO. 24) | 152 | GT, GAimp | 60° C. |
| WMS088 | 5' CAC TAC AAC TAT GCG CTC GC 3' | (SEQ. ID NO. 25) | 5' TCC ATT GGC TTC TCT CTC AA 3' | (SEQ. ID NO. 26) | 121 | GT | 60° C. |
| WMS095 | 5' GAT CAA ACA CAC ACC CCT CC 3' | (SEQ. ID NO. 27) | 5' AAT GCA AAG TGA AAA ACC CG 3' | (SEQ. ID NO. 28) | 121 | CA | 60° C. |
| WMS099 | 5' AAG ATG GAC GTA TGC ATC ACA 3' | (SEQ. ID NO. 29) | 5' GCC ATA TTT GAT GAC GCA TA 3' | (SEQ. ID NO. 30) | 119 | CA | 60° C. |
| WMS102 | 5' TCT CCC ATC CAA CGC CTC 3' | (SEQ. ID NO. 31) | 5' TGT TGG CTT GAC TAT TG 3' | (SEQ. ID NO. 32) | 143 | CT | 60° C. |
| WMS106 | 5' CTG TTC TTG CGT GGC ATT AA 3' | (SEQ. ID NO. 33) | 5' AAT AAG GAC ACA ATT GGG ATG G 3' | (SEQ. ID NO. 34) | 139 | GA | 60° C. |
| WMS107 | 5' ATT AAT ACC TGA GGG AGC TGC 3' | (SEQ. ID NO. 35) | 5' GGT CTC AGG AGC AAG AAC AC 3' | (SEQ. ID NO. 36) | 195 | CT | 60° C. |
| WMS108 | 5' CGA CAA TCG GGT CTT AGC AT 3' | (SEQ. ID NO. 37) | 5' TGC ACA CTT AAA TTA CAT CCG C 3' | (SEQ. ID NO. 38) | 132 | GTimp | 60° C. |
| WMS111 | 5' TCT GTA GGC TCT CTC CGA CTG 3' | (SEQ. ID NO. 39) | 5' ACC TGA TCA GAT CCC ACT CG 3' | (SEQ. ID NO. 40) | 205 | CT, GT | 60° C. |
| WMS112 | 5' CTA AAC ACG ACA GCG GTG G 3' | (SEQ. ID NO. 41) | 5' GAT ATG GGT TGA GCA GCG AG 3' | (SEQ. ID NO. 42) | 101 | CTimp | 55° C. |
| WMS113 | 5' ATT CGA GGT TAG GAG GAA GAG G 3' | (SEQ. ID NO. 43) | 5' GAG GGT CGG CCT ATA AGA CC 3' | (SEQ. ID NO. 44) | 148 | GT | 55° C. |
| WMS114 | 5' ACA AAC AGA AAA TCA AAA CCC G 3' | (SEQ. ID NO. 45) | 5' ATC CAT CGC CAT TGG AGT G 3' | (SEQ. ID NO. 46) | 206 (177) | GA | 60° C. |
| WMS118 | 5' GAT GTT GCC ACT TGA GCA TG 3' | (SEQ. ID NO. 47) | 5' GAT TAG TCA AAT GGA ACA CCC C 3' | (SEQ. ID NO. 48) | 110 | CA | 60° C. |

| WMS Number | WMS Primer Left | WMS Primer Right | Length (bp) in "cs" | Repeat Type | Annealing Temperature |
|---|---|---|---|---|---|
| WMS119 | 5' TGA CTA ACA TCC TTT GTC ACG C 3' (SEQ. ID NO. 49) | 5' CAT GTC TCA ACC ACC CAC AG 3' (SEQ. ID NO. 50) | 181 | GTimp | 55° C. |
| WMS120 | 5' GAT CCA CCT TCC TCT CTC TC 3' (SEQ. ID NO. 51) | 5' GAT TAT ACT GGT GCC GAA AC 3' (SEQ. ID NO. 52) | 139 | CT,CA | 55° C. |
| WMS121 | 5' TCC TCT ACA AAC AAA CAC AC 3' (SEQ. ID NO. 53) | 5' CTC GCA ACT AGA GGT GTA TG 3' (SEQ. ID NO. 54) | 143 | CA | 50° C. |
| WMS122 | 5' GGG TGG GAG AAA GGA GAT G 3' (SEQ. ID NO. 55) | 5' AAA CCA TCC TCC ATC CTG G 3' (SEQ. ID NO. 56) | 149 | CT,CA | 60° C. |
| WMS124 | 5' GCC ATG GCT ATC ACC CAG 3' (SEQ. ID NO. 57) | 5' ACT GTT CGG TGC AAT TTG AG 3' (SEQ. ID NO. 58) | 213 | CT,GTimp | 60° C. |
| WMS126 | 5' CAC ACG CTC CAC CAT GAC 3' (SEQ. ID NO. 59) | 5' GTT GAG TTG ATG CGG GAG G 3' (SEQ. ID NO. 60) | 196 | CA | 60° C. |
| WMS128 | 5' AGC ACA TTT TAA CAC AGA TA 3' (SEQ. ID NO. 61) | 5' ATC TGT GAA ATT TTG AAA AC 3' (SEQ. ID NO. 62) | 176 | CA | 50° C. |
| WMS129 | 5' TCA GTG GGC AAG CTA CAC AG 3' (SEQ. ID NO. 63) | 5' AAA ACT TAG TAG CCG CGT 3' (SEQ. ID NO. 64) | 221 | GTimp | 55° C. |
| WMS130 | 5' AGC TCT GCT TCA CGA GGA AG 3' (SEQ. ID NO. 65) | 5' CTC CTC TTT ATA TCG CGT CCC 3' (SEQ. ID NO. 66) | 113 | GT | 60° C. |
| WMS131 | 5' AAT CCC CAC CGA TTC TTC TC 3' (SEQ. ID NO. 67) | 5' AGT TCG GTC TCT GAT GG 3' (SEQ. ID NO. 68) | 131 | CT | 60° C. |
| WMS132 | 5' TAC CAA ATC GAA ACA CAT CAG 3' (SEQ. ID NO. 69) | 5' CAT ATC AAG GTC TCC TTC CCC 3' (SEQ. ID NO. 70) | 119 | GA,GAA | 60° C. |
| WMS133 | 5' ATC TAA ACA AGA CGG CGG TG 3' (SEQ. ID NO. 71) | 5' ATC TGT GAC AAC CGG TGA GA 3' (SEQ. ID NO. 72) | 118 | CT | 60° C. |
| WMS134 | 5' CAT GGA ACT TAG ACA GAT TG 3' (SEQ. ID NO. 73) | 5' CAG TAC TTG GTA CTG AAC AGG 3' (SEQ. ID NO. 74) | 111 | CA | 60° C. |
| WMS135 | 5' TGT CAA CAT CGT TTT GAA AAG G 3' (SEQ. ID NO. 75) | 5' ACA CTG TCA ACC TGG CAA TG 3' (SEQ. ID NO. 76) | 143 | GA | 55° C. |
| WMS136 | 5' GAC AGC ACC TTG CCC TTT G 3' (SEQ. ID NO. 77) | 5' CAT CGG CAA CAT GCT CAT C 3' (SEQ. ID NO. 78) | 296 | CT | 60° C. |
| WMS140 | 5' ATG GAG ATA TTT GGC CTA CAA C 3' (SEQ. ID NO. 79) | 5' CTT GAC TTC AAG GCG TGA CA 3' (SEQ. ID NO. 80) | 251 | CT | 55° C. |
| WMS144 | 5' TTT GCT GTG CGA CGA AAC ATA C 3' (SEQ. ID NO. 81) | 5' ACT CAC AAA TGT CTA ATA AAA C 3' (SEQ. ID NO. 82) | 200 | GT | 50° C. |
| WMS146 | 5' CCA AAA ACT GCC CCT GCA TG 3' (SEQ. ID NO. 83) | 5' CTC TGG CAT TGC TCC TTG G 3' (SEQ. ID NO. 84) | 162 | GAimp | 60° C. |
| WMS148 | 5' GTG AGG CAG CAA GAG AGA AA 3' (SEQ. ID NO. 85) | 5' CAA AGC TTG ACT CAG ACC AAA 3' (SEQ. ID NO. 86) | 163 | CA | 60° C. |
| WMS149 | 5' CAT TGT TTT CTG CCT CTA GCC 3' (SEQ. ID NO. 87) | 5' CTA GCA TCG AAC CTG AAC AAG 3' (SEQ. ID NO. 88) | 161 | GA | 55° C. |
| WMS153 | 5' GAT CTC GTC ACC CGG AAT TC 3' (SEQ. ID NO. 89) | 5' TGG TAG AGA AGG ACG GAG AG 3' (SEQ. ID NO. 90) | 188 | GA | 60° C. |
| WMS154 | 5' TCA CAG AGA GAG AGG GAG GG 3' (SEQ. ID NO. 91) | 5' ATG CAT TGT ACA TGT GCT GCA 3' (SEQ. ID NO. 92) | 102 | GA | 55° C. |
| WMS155 | 5' CAA TCA TTT CCC CCT CCC 3' (SEQ. ID NO. 93) | 5' AAT CAT TGG AAA TCC ATA TGC C 3' (SEQ. ID NO. 94) | 141 | CT | 60° C. |
| WMS156 | 5' CCA ACC GTG CTA TTA GTC ATT C 3' (SEQ. ID NO. 95) | 5' CAA TGC AGG CCC TCC TAA C 3' (SEQ. ID NO. 96) | 277 | GT | 60° C. |
| WMS157 | 5' GTC GTC GCG GTA AGC TTG 3' (SEQ. ID NO. 97) | 5' GAG TGA ACA CAC GAG GCT TG 3' (SEQ. ID NO. 98) | 106 | CT | 60° C. |

-continued

| WMS Number | WMS Primer Left | WMS Primer Right | Length (bp in "cs") | Repeat Type | Annealing Temperature |
|---|---|---|---|---|---|
| WMS159 | 5' GGG CCA ACA CTG GAA CAC 3' (SEQ. ID NO. 99) | 5' GCA GAA GCT TGT TGG TAG GC 3' (SEQ. ID NO. 100) | 192 | GT | 60° C. |
| WMS160 | 5' TTC AAT TCA GTC TTG GCT TGG 3' (SEQ. ID NO. 101) | 5' CTG CAG GAA AAA AAG TAC ACC C 3' (SEQ. ID NO. 102) | 184 | GA | 60° C. |
| WMS161 | 5' GAT CGA GTG ATG GCA GAT GG 3' (SEQ. ID NO. 103) | 5' TGT GAA TTA CTT GGA CCT GG 3' (SEQ. ID NO. 104) | 154 | CT | 60° C. |
| WMS162 | 5' AGT GGA TCG ACA AGG CTC TG 3' (SEQ. ID NO. 105) | 5' AGA AGA AGC AAA GCC TTC CC 3' (SEQ. ID NO. 106) | 208 | CA | 60° C. |
| WMS163 | 5' ACC TCG ACA GAC CTG GTA CG 3' (SEQ. ID NO. 107) | 5' GTC TTT GTC ACC CGA TGG AC 3' (SEQ. ID NO. 108) | 127 | CT | 55° C. |
| WMS164 | 5' ACA TTT CTC CCC CAT CGT C 3' (SEQ. ID NO. 109) | 5' TTG TAA AAT CGC ATG CG 3' (SEQ. ID NO. 110) | 120 | CT | 55° C. |
| WMS165 | 5' TGC AGT GGT CAG ATG TTT CC 3' (SEQ. ID NO. 111) | 5' CTT TTC TTT CAG ATT GCG CC 3' (SEQ. ID NO. 112) | 199 | GA | 60° C. |
| WMS169 | 5' ACC ACT GCA GAG AAC ACA TAC G 3' (SEQ. ID NO. 113) | 5' GTG CTC TGC TCT AAG TGT GGG 3' (SEQ. ID NO. 114) | 196 | GA | 60° C. |
| WMS174 | 5' GGG TTC CTA TCT GGT AAA TCC C 3' (SEQ. ID NO. 115) | 5' GAC ACA CAT GTT CCT GCC AC 3' (SEQ. ID NO. 116) | 173 | CT | 55° C. |
| WMS179 | 5' AAG TTG AGT TGA TGC GGG AG 3' (SEQ. ID NO. 117) | 5' CCA TGA CCA GCA TCC ACT C 3' (SEQ. ID NO. 118) | 181 | GT | 55° C. |
| WMS180 | 5' ATC CGC CTA AGG AAT AGT GT 3' (SEQ. ID NO. 119) | 5' GAT CGC ACG GGA GAG AGA G 3' (SEQ. ID NO. 120) | 84 | CT | 50° C. |
| WMS181 | 5' TCA TTG GTA ATG AGG AGA GA 3' (SEQ. ID NO. 121) | 5' GAA CCA TTC ATG TGC ATG TC 3' (SEQ. ID NO. 122) | 135 | GA | 50° C. |
| WMS182 | 5' TGA TGT AGT GAG CCC ATA GGC 3' (SEQ. ID NO. 123) | 5' TTG CAC ACA GCC AAA TAA GG 3' (SEQ. ID NO. 124) | 165 | CT | 60° C. |
| WMS186 | 5' GCA GAG CCT GGT TCA AAA AG 3' (SEQ. ID NO. 125) | 5' AAT TGT GAT GAT TTG GGG 3' (SEQ. ID NO. 126) | 140 | GA | 60° C. |
| WMS189 | 5' AGG AGC AGC GGA ACG AAC 3' (SEQ. ID NO. 127) | 5' CGC CTC TAG CGA GAG CTA TG 3' (SEQ. ID NO. 128) | 117 | CA | 55° C. |
| WMS190 | 5' GTG CTT GCT GAG CTA TGA GTC 3' (SEQ. ID NO. 129) | 5' AGA AAT ACG GAA ACC CAC CC 3' (SEQ. ID NO. 130) | >201 | CT,GT | 60° C. |
| WMS191 | 5' AGA CTG TTG TTT GCG GGC 3' (SEQ. ID NO. 131) | 5' GTG CCA CGT GGT ACC TTT G 3' (SEQ. ID NO. 132) | 128 | CT | 60° C. |
| WMS192 | 5' GGT TTT CTT TCA GAT TGC GC 3' (SEQ. ID NO. 133) | 5' TAG CAC GAC AGT TGT ATG CAT G 3' (SEQ. ID NO. 134) | 191 | CT | 60° C. |
| WMS193 | 5' CTT TGT GCA CCT CTC TCT CC 3' (SEQ. ID NO. 135) | 5' CGT TGT CTA ATC TTG CCT TGC 3' (SEQ. ID NO. 136) | 171 | CT,CA | 60° C. |
| WMS194 | 5' GAT CTG CTC TAC TCT CCT CC 3' (SEQ. ID NO. 137) | 5' AAT TGT GTT GAT GAT TTG GGG 3' (SEQ. ID NO. 138) | 131 | CT | 50° C. |
| WMS195 | 5' AGG TGC CGT CGC GTC TAC 3' (SEQ. ID NO. 139) | 5' CGA CGC AGA ACT TAA ACA AG 3' (SEQ. ID NO. 140) | 108 | CT | 60° C. |
| WMS197 | 5' GAG AAA GAG GTC TGG AGG TCG 3' (SEQ. ID NO. 141) | 5' ACC CCC CAC GTC AGA GAG 3' (SEQ. ID NO. 142) | 126 | CT | 60° C. |
| WMS198 | 5' TTG AAC CGG AAG GAG TAC AG 3' (SEQ. ID NO. 143) | 5' CAA AAT GCA CAA GAA TGG AGG 3' (SEQ. ID NO. 144) | 130 | CA | 60° C. |
| WMS200 | 5' TCA ACG GAA CAG AGA ATG AGC G 3' (SEQ. ID NO. 145) | 5' GAC CTG ATG AGA AGC AC 3' (SEQ. ID NO. 146) | 250 | CT | 60° C. |

-continued

| WMS Number | WMS Primer Left | WMS Primer Right | Length (bp in "cs") | Repeat Type | Annealing Temperature |
|---|---|---|---|---|---|
| WMS203 | 5' CCC AAA GCA GCG CAA GC 3' (SEQ. ID NO. 147) | 5' ACC AAT GCT ATC GGC TCG 3' (SEQ. ID NO. 148) | 139 | CA,GA | 55° C. |
| WMS205 | 5' CGA CCC GGT TCA CTT CAG 3' (SEQ. ID NO. 149) | 5' AGT CGC CGT TGT ATA GTG CC 3' (SEQ. ID NO. 150) | 152 | CT | 60° C. |
| WMS210 | 5' TGC ATC AAG AAT AGT GTG GAA G 3' (SEQ. ID NO. 151) | 5' TGA GAG GAA GGC TCA CAC CT 3' (SEQ. ID NO. 152) | 192 | GA | 60° C. |
| WMS212 | 5' AAG CAA CAT TTG CTG CAA TG 3' (SEQ. ID NO. 153) | 5' TGC AGT TAA CTT GTT GAA AGG A 3' (SEQ. ID NO. 154) | 104 | CT | 60° C. |
| WMS213 | 5' TGC CTG GCT CGT TCT ATC TC 3' (SEQ. ID NO. 155) | 5' CTA GCT TAG CAC TGT CGC CC 3' (SEQ. ID NO. 156) | 184 | GA | 60° C. |
| WMS218 | 5' CGG CAA ACG GAT ATC GAC 3' (SEQ. ID NO. 157) | 5' AAC AGT AAC TCT CGC CAT AGC C 3' (SEQ. ID NO. 158) | 149 | CT | 60° C. |
| WMS219 | 5' GAT GAG CGA CAC CTA GCC TC 3' (SEQ. ID NO. 159) | 5' GGG GTC CGA GTC CAC AAC 3' (SEQ. ID NO. 160) | 181 | GAimp | 60° C. |
| WMS224 | 5' TGA GTC CAG CAC TGC 3' (SEQ. ID NO. 161) | 5' CAA CAT CCG CTC GTA TTC AA 3' (SEQ. ID NO. 162) | 142 | CT | 50° C. |
| WMS228 | 5' TCA TAT GCA CCT CTT TCC TAG G 3' (SEQ. ID NO. 163) | 5' GTG TGC CAC CTT TGA CGT C 3' (SEQ. ID NO. 164) | 210 | CT,CA | 60° C. |
| WMS231 | 5' AGC TCG GGA TGA AGC GTG 3' (SEQ. ID NO. 165) | 5' GAT CCG CCG CTG CGT TT 3' (SEQ. ID NO. 166) | 130 | GAimp | 60° C. |
| WMS232 | 5' ATC TCA ACG GCA AGC CG 3' (SEQ. ID NO. 167) | 5' CTG ATG CAA GCA ATC CAC C 3' (SEQ. ID NO. 168) | 141 | GA | 55° C. |
| WMS233 | 5' TCA AAA CAT AAA TGT TCA TTG GA 3' (SEQ. ID NO. 169) | 5' TCA ACC GTG TGT AAT TTT GTC C 3' (SEQ. ID NO. 170) | 261 | CT | 60° C. |
| WMS234 | 5' GAG TCC TGA TGT GAA GCT GTT G 3' (SEQ. ID NO. 171) | 5' CTC ATT GGG GTG TGT ACG TG 3' (SEQ. ID NO. 172) | 241 | CT,CA | 55° C. |
| WMS237 | 5' GAA TCA CTT GTG AAG CAT CTG G 3' (SEQ. ID NO. 173) | 5' CTG GAT GCA TCA CAT CCA AC 3' (SEQ. ID NO. 174) | 137 | CT | 55° C. |
| WMS238 | 5' TCG CTT CTA CCG CTC ACC 3' (SEQ. ID NO. 175) | 5' AGT GCC TTG CCG AGG TC 3' (SEQ. ID NO. 176) | 204 | CT,GT,GGGT | 55° C. |
| WMS241 | 5' TCT TCC AAC TAA AGC ATA GC 3' (SEQ. ID NO. 177) | 5' CTT CCA TGG ACT ACA TAC TAG 3' (SEQ. ID NO. 178) | 146 | GA | 55° C. |
| WMS242 | 5' TCC AAG GCA GTA GGC AGG 3' (SEQ. ID NO. 179) | 5' TGT TGT TGG CCT GTA TGC AT 3' (SEQ. ID NO. 180) | 142 | GA | 55° C. |
| WMS244 | 5' GGC AGC TGA GGC AAT CTG 3' (SEQ. ID NO. 181) | 5' TTT GGA CAT TTC CCA GCG 3' (SEQ. ID NO. 182) | 227 | CAimp | 60° C. |
| WMS245 | 5' CAG CGC AGT TAG CTC GC 3' (SEQ. ID NO. 183) | 5' ATC TGT CCA TTC GAG CGC 3' (SEQ. ID NO. 184) | 141 | CT | 60° C. |
| WMS247 | 5' GCA ATC TTT TTT CTG ACC ACG 3' (SEQ. ID NO. 185) | 5' ATG TGC ATG TCG GAC GC 3' (SEQ. ID NO. 186) | 158 | GA | 55° C. |
| WMS248 | 5' AGG ACT TCC GCA CCC TG 3' (SEQ. ID NO. 187) | 5' TGG CGT GGT CTA AAT GGA C 3' (SEQ. ID NO. 188) | 185 | CA | 60° C. |
| WMS249 | 5' CAA ATG GAT CGA GAA AGG GA 3' (SEQ. ID NO. 189) | 5' CTG CCA TTT TTC TGG ATC TAC C 3' (SEQ. ID NO. 190) | 177 | GAimp | 60° C. |
| WMS251 | 5' CAA CTG GTT GCT ACA CAA GCA 3' (SEQ. ID NO. 191) | 5' GGG ATG TCT GTT CCA TCT TAG 3' (SEQ. ID NO. 192) | 103 | CA | 55° C. |
| WMS255 | 5' CAA CTG TAC GGT TTC ATT GC 3' (SEQ. ID NO. 193) | 5' TCT GCC GTA AGT CGC CTC 3' (SEQ. ID NO. 194) | 148 | GA | 55° C. |
| WMS257 | 5' AGA GTG CAT GGT GGG ACG 3' (SEQ. ID NO. 195) | 5' CCA AGA CGA TGC TGA AGT CA 3' (SEQ. ID NO. 196) | 192 | GT | 60° C. |

| WMS Number | WMS Primer Left | WMS Primer Right | Length (bp in "cs") | Repeat Type | Annealing Temperature |
|---|---|---|---|---|---|
| WMS258 | 5' GAT CGC TTC ATC TCT CTC TCT C 3' (SEQ. ID NO. 197) | 5' GTA CAC GCC GTA GGC CC 3' (SEQ. ID NO. 198) | >81 | CT | 60° C. |
| WMS259 | 5' AGG GAA AAG ACA TCT TTT TTT TC 3' (SEQ. ID NO. 199) | 5' CGA CCG ACT TCG GGT TC 3' (SEQ. ID NO. 200) | 105 | GA | 55° C. |
| WMS260 | 5' GCC CCC TTG CAC AAA TC 3' (SEQ. ID NO. 201) | 5' CGC AGC TAC AGG AGG CC 3' (SEQ. ID NO. 202) | 157 | GA | 55° C. |
| WMS261 | 5' CTC CCT GTA CGC CTA AGG C 3' (SEQ. ID NO. 203) | 5' CTC GCG CTA CCT AGC CAT TG 3' (SEQ. ID NO. 204) | 192 | CT | 55° C. |
| WMS263 | 5' TCT GCC GTA AGT CGC CTC 3' (SEQ. ID NO. 205) | 5' GGT TTC ATT GCT TGC CCT AA 3' (SEQ. ID NO. 206) | 134 | CT | 55° C. |
| WMS264 | 5' GAG AAA CAT GCC GAA CAA CA 3' (SEQ. ID NO. 207) | 5' GCA TGC ATG AGA ATA GGA ACT G 3' (SEQ. ID NO. 208) | 219 | CA | 60° C. |
| WMS265 | 5' TGT TGC GGA TGG TCA CTA TT 3' (SEQ. ID NO. 209) | 5' GAG TAC TGC GTA CGT CTC TGC 3' (SEQ. ID NO. 210) | 200 | CT | 55° C. |
| WMS268 | 5' AGG GGA TAT GTT GTC ACT CCA 3' (SEQ. ID NO. 211) | 5' TTA TGT GAT TGC CAA AGT TTG GGA CA 3' (SEQ. ID NO. 212) | 241 | GAimp | 55° C. |
| WMS269 | 5' TGC ATA TAA ACA GTC ACA CAC CC 3' (SEQ. ID NO. 213) | 5' TTT GAG CTC TAG CTT TTG GGA CA 3' (SEQ. ID NO. 214) | >148 | CA | 60° C. |
| WMS271 | 5' CAA GAT CGT GGA GCC AGC 3' (SEQ. ID NO. 215) | 5' AGC TGC CAA AAC TTA AAA GGC CC 3' (SEQ. ID NO. 216) | 162 | CT,GA | 60° C. |
| WMS272 | 5' TGC TCT TTG GCG AAT ATA TGG 3' (SEQ. ID NO. 217) | 5' GTT CAA AAC AAA TTA AAA GGC CC 3' (SEQ. ID NO. 218) | 140 | CA | 55° C. |
| WMS273 | 5' ATT GGA CGG ACA GAT GCT TT 3' (SEQ. ID NO. 219) | 5' AGC AGT GAG AAA GGG GAT C 3' (SEQ. ID NO. 220) | 167 | GA | 55° C. |
| WMS274 | 5' AAC TTG CAA AAC TGT TCT GA 3' (SEQ. ID NO. 221) | 5' TAT TTG AAG CGG TTT GAT TT 3' (SEQ. ID NO. 222) | 179 | GT | 50° C. |
| WMS275 | 5' AAT TTT CTT CCT CAC TTA TTC T 3' (SEQ. ID NO. 223) | 5' AAC AAA AAA TTA GGG CC 3' (SEQ. ID NO. 224) | 107 | CT | 50° C. |
| WMS276 | 5' ATT TGC CTG AAG AAA ATA TT 3' (SEQ. ID NO. 225) | 5' AAT TTC ACT GCA TAC ACA AG 3' (SEQ. ID NO. 226) | 99 | CT | 55° C. |
| WMS278 | 5' GTT GCT TCA TGA ACG CTC AA 3' (SEQ. ID NO. 227) | 5' CTG CCC AAT TTT CTC CAC TC 3' (SEQ. ID NO. 228) | 241 | GTimpGAimp | 55° C. |
| WMS281 | 5' CGG CCA TAT TTC TGT AAG TAT GC 3' (SEQ. ID NO. 229) | 5' GCA GGT GAA AAT GGC CGG AC 3' (SEQ. ID NO. 230) | 135 | CT | 60° C. |
| WMS282 | 5' TTG GCC GTG TAA GGC AG 3' (SEQ. ID NO. 231) | 5' TCT CAT TCA CAC ACA CTA GC 3' (SEQ. ID NO. 232) | 220 | GA | 55° C. |
| WMS284 | 5' AAT GAA AAA ACA CTT GCG TGG 3' (SEQ. ID NO. 233) | 5' GCA CAT TTT TCA CTT TCG GG 3' (SEQ. ID NO. 234) | 123 | GA | 60° C. |
| WMS285 | 5' ATG ACC CTT CCA AAC AC 3' (SEQ. ID NO. 235) | 5' ATC GAC CGG GAT TAT GCC 3' (SEQ. ID NO. 236) | 243 | GA | 60° C. |
| WMS291 | 5' CAT CCC TAC GCC ACT CTG C 3' (SEQ. ID NO. 237) | 5' AAT GGT ATC TAT TCC GAC CCG 3' (SEQ. ID NO. 238) | >158 | CA | 60° C. |
| WMS292 | 5' TCA CCG TGG TCA CCG AC 3' (SEQ. ID NO. 239) | 5' CCA CCG AGC CGA TAA TGT AC 3' (SEQ. ID NO. 240) | 220 | CT | 60° C. |
| WMS293 | 5' TAC TGG TTC ACA TTG GTG CG 3' (SEQ. ID NO. 241) | 5' TCG CCA TCA CTC GTT CAA G 3' (SEQ. ID NO. 242) | 201 | CA | 55° C. |
| WMS294 | 5' GGA TTG GAG TTA AGA GAG AAC CG 3' (SEQ. ID NO. 243) | 5' GCA GAG TGA TCA ATG TCC AGA 3' (SEQ. ID NO. 244) | 100 | GAimp | 55° C. |

-continued

| WMS Number | WMS Primer Left | | WMS Primer Right | | Length (bp) in "cs" | Repeat Type | Annealing Temperature |
|---|---|---|---|---|---|---|---|
| WMS295 | 5' GTG AAG CAG ACC CAC AAC AC 3' | (SEQ. ID NO. 245) | 5' GAC GGC TGC GAC GTA GAG 3' | (SEQ. ID NO. 246) | 258 | GA | 60° C. |
| WMS296 | 5' AAT TCA ACC TAC CAA TCT CTG 3' | (SEQ. ID NO. 247) | 5' GCC TAA TAA ACT GAA AAC GAG 3' | (SEQ. ID NO. 248) | 149 | CT | 55° C. |
| WMS297 | 5' ATC GTC ACG TAT TTT GCA ATG 3' | (SEQ. ID NO. 249) | 5' TGC GTA AGT CTA GCA TTT TCT G 3' | (SEQ. ID NO. 250) | 150 | GT,GA | 55° C. |
| WMS299 | 5' ACT ACT TAG GCC TCC CGC C 3' | (SEQ. ID NO. 251) | 5' TGA CCC ACT TGC AAT TCA TC 3' | (SEQ. ID NO. 252) | 208 | GA,TAG | 55° C. |
| WMS301 | 5' GAG GAG TAA GAC ACA TGC CC 3' | (SEQ. ID NO. 253) | 5' GTG GCT GGA GAT TCA GGT TC 3' | (SEQ. ID NO. 254) | 204 | GA,G | 55° C. |
| WMS302 | 5' GCA AGA AGC AAC AGC AGT AAC 3' | (SEQ. ID NO. 255) | 5' CAG ATG CTC TTC TCT GCT GG 3' | (SEQ. ID NO. 256) | 180 (340) | GA | 60° C. |
| WMS304 | 5' AGG AAA CAG AAA TAT CGC GG 3' | (SEQ. ID NO. 257) | 5' AGG ACT GTG GGG AAT GAA TG 3' | (SEQ. ID NO. 258) | 217 | CT | 55° C. |
| WMS311 | 5' TCA CGT GGA AGA CGC TCC 3' | (SEQ. ID NO. 259) | 5' CTA CGT GCA CCA CCA TTT TG 3' | (SEQ. ID NO. 260) | 151 | GA | 60° C. |
| WMS312 | 5' ATC GCA TGA TGC ACG TAG AG 3' | (SEQ. ID NO. 261) | 5' ACA TGC ATG CCT ACC TAA TGG 3' | (SEQ. ID NO. 262) | 235 | GA | 60° C. |
| WMS313 | 5' CCG CCC TCA TTA AGT TTC AC 3' | (SEQ. ID NO. 263) | 5' TTT GAC AAG TAC ACG AGT CTG C 3' | (SEQ. ID NO. 264) | 156 | CT,GT | 55° C. |
| WMS314 | 5' AGG AGC TCC TCT GTG CCA C 3' | (SEQ. ID NO. 265) | 5' TTC GGG ACT CTC TTC CCT G 3' | (SEQ. ID NO. 266) | 170 | CT | 55° C. |
| WMS316 | 5' CAT GGA CAT TTT ACC ACA AGA C 3' | (SEQ. ID NO. 267) | 5' TGC GTG TGG TCC ACC TC 3' | (SEQ. ID NO. 268) | 176 | AT,GT | 55° C. |
| WMS319 | 5' TGC TGT ACA AGT GTT CAC G 3' | (SEQ. ID NO. 269) | 5' CGG GTG CTG TGT GTA ATG AC 3' | (SEQ. ID NO. 270) | 200 | CT | 55° C. |
| WMS320 | 5' GGT ACT ATG GAA GGT GAG G 3' | (SEQ. ID NO. 271) | 5' ATC TTT GCA AGG ATT GCC C 3' | (SEQ. ID NO. 272) | >263 | GT,GA | 55° C. |
| WMS321 | 5' CGA GAT CAC GGT GTG C 3' | (SEQ. ID NO. 273) | 5' TGT TGC ATG CGA TCA TGC 3' | (SEQ. ID NO. 274) | 265 | GT,GAimp | 60° C. |
| WMS322 | 5' CAA TGT GGA GAC ACC AAA AC 3' | (SEQ. ID NO. 275) | 5' TGC AGA AAA CCA ACA AGG G 3' | (SEQ. ID NO. 276) | 119 | GA | 55° C. |
| WMS325 | 5' TCA CAA TTT CTG TCG TTC TCC 3' | (SEQ. ID NO. 277) | 5' TTT TTA CGC GTC AAC GAC G 3' | (SEQ. ID NO. 278) | 131 | CT | 55° C. |
| WMS328 | 5' GCA ATC CAC AGT CTT CAC G 3' | (SEQ. ID NO. 279) | 5' CAC AAA CTC TTC ATG TAC ACA TGT GCG 3' | (SEQ. ID NO. 280) | 193 | GT | 55° C. |
| WMS330 | 5' TTG CTA TCC ATG TGC CAG AG 3' | (SEQ. ID NO. 281) | 5' ACA TGT TTC GGA AAG AGT CAG GCC 3' | (SEQ. ID NO. 282) | 165 | GTT | 55° C. |
| WMS332 | 5' AGC CAG CAA GTC ACC AAA AC 3' | (SEQ. ID NO. 283) | 5' AGT GCT GGA AAG AGT TTA GAA GC 3' | (SEQ. ID NO. 284) | 231 | GA | 60° C. |
| WMS333 | 5' GCC CGG TCA TGT AAA ACG 3' | (SEQ. ID NO. 285) | 5' TGT TCA GTT TAG CTA TC 3' | (SEQ. ID NO. 286) | 150 | GA | 55° C. |
| WMS334 | 5' AAT TTC AAA AAG GAG AGA GA 3' | (SEQ. ID NO. 287) | 5' AAC ATG TGT TTT TAG CTA TC 3' | (SEQ. ID NO. 288) | 123 | GA | 50° C. |
| WMS335 | 5' CGT ACT CCA CTC CAC ACG G 3' | (SEQ. ID NO. 289) | 5' CGG TCC AAG TGC CTT TC 3' | (SEQ. ID NO. 290) | 187 (225) | GA,GCGT | 55° C. |
| WMS336 | 5' CCC TTT AAT CTC GCT CCC TC 3' | (SEQ. ID NO. 291) | 5' GTC TCT TTC TCG TAC TTC CAG G 3' | (SEQ. ID NO. 292) | 108 | CT | 55° C. |
| WMS337 | 5' CCT CTT CCT CCC TCA CTT AGC 3' | (SEQ. ID NO. 293) | 5' TGC TAA CTG GCC TTT GCC 3' | (SEQ. ID NO. 294) | 183 | CT,CACT,CA | 55° C. |

| WMS Number | WMS Primer Left | WMS Primer Right | Length (bp) in "cs" | Repeat Type | Annealing Temperature |
|---|---|---|---|---|---|
| WMS339 | 5' AAT TTT CTT CCT CAC TTA TT 3' (SEQ. ID NO. 295) | 5' AAA CGA ACA ACC ACT CAA TC 3' (SEQ. ID NO. 296) | 159 | CT | 60° C. |
| WMS340 | 5' GCA ATC TTT CTG ACC ACG 3' (SEQ. ID NO. 297) | 5' ACG AGG CAA GAA CAC ACA TG 3' (SEQ. ID NO. 298) | 132 | GA | 60° C. |
| WMS341 | 5' TTC AGT GGT AGC GGT CGA G 3' (SEQ. ID NO. 299) | 5' CCG ACA TCT CAT GGA TCC AC 3' (SEQ. ID NO. 300) | 133 (150) | CT | 55° C. |
| WMS342 | 5' TAT CCA GAG CAG ACG GAC G 3' (SEQ. ID NO. 301) | 5' GGT CTA GCT TCG ACG ACA CT 3' (SEQ. ID NO. 302) | 169 | CT | 55° C. |
| WMS344 | 5' CAA GGA AAT AGG CGG TAA TT 3' (SEQ. ID NO. 303) | 5' ATT TGA GTC TGA AGT TTG CA 3' (SEQ. ID NO. 304) | 131 | CT | 55° C. |
| WMS346 | 5' CAA GCA AGG TTT CGT TTT ATC C 3' (SEQ. ID NO. 305) | 5' GCA TGT GGT CCA TGT ACT GC 3' (SEQ. ID NO. 306) | 203 | AT,GT | 55° C. |
| WMS349 | 5' GGC TTC CAG AAA ACA ACA GG 3' (SEQ. ID NO. 307) | 5' ATC GGT GCG TAC CAT CCT AC 3' (SEQ. ID NO. 308) | 230 | GA | 55° C. |
| WMS350 | 5' ACC TCA TCC ACA TGT TCT ACG 3' (SEQ. ID NO. 309) | 5' GCA TGG ATA GGA CGC CC 3' (SEQ. ID NO. 310) | 146 | CT | 55° C. |
| WMS353 | 5' CCA TGT TGA GTA GGT TCA GCC 3' (SEQ. ID NO. 311) | 5' CTT GGC CAG AAG CTA CGA AC 3' (SEQ. ID NO. 312) | 179 | GCCT,CT | 60° C. |
| WMS356 | 5' AGC GTT CTT GGG AAT TAG AGA 3' (SEQ. ID NO. 313) | 5' CCA ATC AGC CTG CAA CAA C 3' (SEQ. ID NO. 314) | 224 | GA | 55° C. |
| WMS357 | 5' TAT GGT CAA AGT TGG ATC ACG 3' (SEQ. ID NO. 315) | 5' AGG CTG GTT CAG CCT CTC TTC AG 3' (SEQ. ID NO. 316) | 123 | GA | 55° C. |
| WMS358 | 5' AAA CAG CGG ATT TCA TCG AG 3' (SEQ. ID NO. 317) | 5' TCC GCT GTT CTT CTG ATC TC 3' (SEQ. ID NO. 318) | 164 | GAimp | 55° C. |
| WMS359 | 5' ACA ATT GCA ACA GGT CAT GGG 3' (SEQ. ID NO. 319) | 5' TAC TTG TGT TCT GGG ACA ATG G 3' (SEQ. ID NO. 320) | 217 | CT,CTTimp | 55° C. |
| WMS361 | 5' GTA ACT TGT TGC CAA AGG GG 3' (SEQ. ID NO. 321) | 5' ACA AAG ATG GAG AGC GAG ACA 3' (SEQ. ID NO. 322) | 126 | GAimp | 60° C. |
| WMS368 | 5' CCA TTT CAC CTA ATG CCT GC 3' (SEQ. ID NO. 323) | 5' AAT AAA ACC ATG AGC TCA CTT GC 3' (SEQ. ID NO. 324) | 249 | AT | 60° C. |
| WMS369 | 5' CTG CAG GCC ATG ATG ATG 3' (SEQ. ID NO. 325) | 5' ACC GTG GGT GTT GTG AGC 3' (SEQ. ID NO. 326) | 188 | CTimp | 60° C. |
| WMS371 | 5' GAC CAA GAT ATT CAA ACT GGC C 3' (SEQ. ID NO. 327) | 5' AGC TCA GCT TGC TTG GTA CC 3' (SEQ. ID NO. 328) | 170 | CA,GA | 60° C. |
| WMS372 | 5' AAT AGA GCC CTG GGA CTG GG 3' (SEQ. ID NO. 329) | 5' GAA GGA CGA CAT TCC ACC TG 3' (SEQ. ID NO. 330) | >329 | GA | 60° C. |
| WMS374 | 5' ATA GTG TGT TGC ATG CTG TGT 3' (SEQ. ID NO. 331) | 5' TCT AAT TAG CGT TGG CTG CC 3' (SEQ. ID NO. 332) | 213 | GT | 60° C. |
| WMS375 | 5' ATT GGC GAC TCT AGC ATA TAC G 3' (SEQ. ID NO. 333) | 5' GGG ATG TCT GTT CCA TCT TAG C 3' (SEQ. ID NO. 334) | 156 | CA | 55° C. |
| WMS376 | 5' GGG CTA GAA AAC AGG AAG GC 3' (SEQ. ID NO. 335) | 5' TCT CCC GGA GGG TAG GAG 3' (SEQ. ID NO. 336) | 147 | CA,GAimp | 60° C. |
| WMS382 | 5' GTC AGA TAA CGC CGT CCA AT 3' (SEQ. ID NO. 337) | 5' CTA CGT GCA CCA CCA TTT TG 3' (SEQ. ID NO. 338) | 115 | GA | 60° C. |
| WMS383 | 5' ACG CCA GTT GAT CCG TAA AC 3' (SEQ. ID NO. 339) | 5' GAC ATC AAT AAC CGT GGA TGG 3' (SEQ. ID NO. 340) | 195 | GT | 60° C. |
| WMS384 | 5' TTT TCA TTG TGC CCT CTA CT 3' (SEQ. ID NO. 341) | 5' GCC AAG TTT CTT AGC TAG TTA A 3' (SEQ. ID NO. 342) | 204 | GTimp | 55° C. |

| WMS Number | WMS Primer Left | WMS Primer Right | Length (bp) in "cs" | Repeat Type | Annealing Temperature |
|---|---|---|---|---|---|
| WMS388 | 5' CTA CAA TTC GAA GGA GAG GGG 3' (SEQ. ID NO. 343) | 5' CAC CGC GTC AAC TAC TTA AGC 3' (SEQ. ID NO. 344) | 162 | CT,CA,CA, | 60° C. |
| WMS389 | 5' ATC ATG TCG ATC TCC TTG ACG 3' (SEQ. ID NO. 345) | 5' TGC CAT GCA CAT TAG CAG AT 3' (SEQ. ID NO. 346) | 130 | CT,GT | 60° C. |
| WMS390 | 5' AAG TTT CAC ACA AGA TCT CTC C 3' (SEQ. ID NO. 347) | 5' TGA CAA GTA CAC GAG TCT GC 3' (SEQ. ID NO. 348) | 143 | CT,GT | 55° C. |
| WMS391 | 5' ATA GCG AAG TCT CCC TAC TCC A 3' (SEQ. ID NO. 349) | 5' ATG TGC ATG TCG GAC GC 3' (SEQ. ID NO. 350) | 150 | CA,GA | 55° C. |
| WMS393 | 5' TCA TCT GCT ATT TGT GCT ACA 3' (SEQ. ID NO. 351) | 5' TCA AAT ACA CCA ATG TGC C 3' (SEQ. ID NO. 352) | 107 | CA | 55° C. |
| WMS395 | 5' TAC AAC CGC AAG TAA TGC CA 3' (SEQ. ID NO. 353) | 5' TAC CAA CAC CCT AGC CCT TG 3' (SEQ. ID NO. 354) | 147 | CA | 60° C. |
| WMS397 | 5' TGT CAT GGA TTA TTT GGT CGG 3' (SEQ. ID NO. 355) | 5' CTG CAC TCT CGG TAT ACC AGC 3' (SEQ. ID NO. 356) | 179 | CT | 55° C. |
| WMS400 | 5' GTG CTG CCA CCA CTT GC 3' (SEQ. ID NO. 357) | 5' TGT AGG CAC TGC TTG GGA G 3' (SEQ. ID NO. 358) | 139 | CA | 60° C. |
| WMS403 | 5' CGA CAT TGG CTT CGG TG 3' (SEQ. ID NO. 359) | 5' ATA AAA CAG TGC GGT CCA GG 3' (SEQ. ID NO. 360) | 133 | CA | 55° C. |
| WMS408 | 5' TCG ATT TAT TTG GGC CAC TG 3' (SEQ. ID NO. 361) | 5' GTA TAA TTC GTT CAC AGC ACG C 3' (SEQ. ID NO. 362) | 176 | CA | 55° C. |
| WMS410 | 5' GCT TGA GAC CGG CAC AGT 3' (SEQ. ID NO. 363) | 5' CGA GAC CTT GAG GGT CTA GA 3' (SEQ. ID NO. 364) | 334 | CA | 55° C. |
| WMS411 | 5' CCC ATA CGA TGA TGT GTT TCC 3' (SEQ. ID NO. 365) | 5' CAA ACG GAA CAT GGC GGT CCC 3' (SEQ. ID NO. 366) | 148 | CT | 55° C. |
| WMS412 | 5' ATC AAC AAG GTT TGT GTG TTG G 3' (SEQ. ID NO. 367) | 5' ATG AAA CGC GTC GAC CTC CC 3' (SEQ. ID NO. 368) | 121 | GA | 55° C. |
| WMS413 | 5' TGC TTG TCT AGA TTG CTT GGG 3' (SEQ. ID NO. 369) | 5' GAT CGT CTC GTC CTT GGC A 3' (SEQ. ID NO. 370) | 94 | GA | 60° C. |
| WMS415 | 5' GAT CTC CCA TGT CCG CC 3' (SEQ. ID NO. 371) | 5' CGA CAG TCG TCA CTT GCC TA 3' (SEQ. ID NO. 372) | 131 | GAimp | 55° C. |
| WMS425 | 5' GAG CCC ACA AGC TGG CA 3' (SEQ. ID NO. 373) | 5' TCG TTC TCC CAA GGC TTG 3' (SEQ. ID NO. 374) | >143 | CT | 60° C. |
| WMS427 | 5' AAA CTT AGA ACT GTA ATT TCA GA 3' (SEQ. ID NO. 375) | 5' AGT GTG TTC ATT TGA CAG TT 3' (SEQ. ID NO. 376) | 215 | CA | 50° C. |
| WMS428 | 5' CGA GGC AGC GAG GAT TT 3' (SEQ. ID NO. 377) | 5' TTC TCC ACT AGC CCC GC 3' (SEQ. ID NO. 378) | 143 | GA | 60° C. |
| WMS429 | 5' TTG TAC ATT AAG TTC CCA T 3' (SEQ. ID NO. 379) | 5' TTT AAG GAC CTA CAT GAC AC 3' (SEQ. ID NO. 380) | 221 (290) | CT | 50° C. |
| WMS434 | 5' ATG AGT TCC GCC AAA GAA TG 3' (SEQ. ID NO. 381) | 5' ACG AAA TAC ACA AGT GGG ACA 3' (SEQ. ID NO. 382) | 216 | GT | 55° C. |
| WMS437 | 5' GAT CAA GAC TTT TGT ATC TCT C 3' (SEQ. ID NO. 383) | 5' GAT GTC CAA CAG TTA GCT TA 3' (SEQ. ID NO. 384) | 109 | CT | 50° C. |
| WMS440 | 5' CCT ATG GTC TCC ATC ATG AGG 3' (SEQ. ID NO. 385) | 5' TCA TGT CAA TTT ATA AAT TCC ACC 3' (SEQ. ID NO. 386) | 112 | CT | 55° C. |
| WMS443 | 5' GGG TCT TCA TCC GGA ACT CT 3' (SEQ. ID NO. 387) | 5' CCA TGA CAC TTG CTG GTA GTG A 3' (SEQ. ID NO. 388) | 134 | CA,GA | 50° C. |
| WMS445 | 5' TTT GTT GGG GGT TAG GAT TAG 3' (SEQ. ID NO. 389) | 5' CCT TAA CAC TTG CTG GTA GTG A 3' (SEQ. ID NO. 390) | 192 | CT | 55° C. |
| WMS448 | 5' AAA CCA TAT TGG GAG GAA AGG 3' (SEQ. ID NO. 391) | 5' CAC ACG ATG GCA TCA CAT TTG TG 3' (SEQ. ID NO. 392) | 231 | GA | 60° C. |

-continued

| WMS Number | WMS Primer Left | WMS Primer Right | Length (bp) in "cs" | Repeat Type | Annealing Temperature |
|---|---|---|---|---|---|
| WMS455 | 5' ATT CGG TTC GCT AGC TAC CA 3' (SEQ. ID NO. 393) | 5' ACG GAG AGC AAC CTG CC 3' (SEQ. ID NO. 394) | 151 | GTimp | 55° C. |
| WMS456 | 5' TCT GAA CAT TAC ACA ACC CTG A 3' (SEQ. ID NO. 395) | 5' TGC TCT CTC TGA ACC TGA AGC 3' (SEQ. ID NO. 396) | 132 | GA | 55° C. |
| WMS458 | 5' AAT GGC AAT TGG AAG ACA TAG C 3' (SEQ. ID NO. 397) | 5' TTC GCA ATG TTG ATT TGG C 3' (SEQ. ID NO. 398) | 113 | CA | 60° C. |
| WMS459 | 5' ATG GAG TGG TCA CAC TTT GAA 3' (SEQ. ID NO. 399) | 5' AGC TTC TCT GAC CAA CTT CTC G 3' (SEQ. ID NO. 400) | >138 | GA | 55° C. |
| WMS469 | 5' CAA CTC AGT GCT CAC ACA ACG 3' (SEQ. ID NO. 401) | 5' CGA TAA CCA CTC ATC CAC ACC 3' (SEQ. ID NO. 402) | >156 | Cr | 60° C. |
| WMS471 | 5' CGG CCC TAT CAT GGC TG 3' (SEQ. ID NO. 403) | 5' GCT TGC AAG TTC CAT TTT GC 3' (SEQ. ID NO. 404) | 149 | CA | 60° C. |
| WMS473 | 5' TCA TAC GGG TAT GGT TGG AC 3' (SEQ. ID NO. 405) | 5' CAC CCC CTT GTT GGT CAC 3' (SEQ. ID NO. 406) | 220 | GTimp | 55° C. |
| WMS476 | 5' ATG GGT TCG TAC TAA CAT CAG C 3' (SEQ. ID NO. 407) | 5' TTG CTG GTA GCT TCA ATC CC 3' (SEQ. ID NO. 408) | >194 | GAimp | 60° C. |
| WMS480 | 5' TGC TAC TTG TAC AGA GGA C 3' (SEQ. ID NO. 409) | 5' CCG AAT TGT CCG CCA TAG 3' (SEQ. ID NO. 410) | 188 | CT,CA | 60° C. |
| WMS484 | 5' ACA TCG CTC TTC ACA AAC CC 3' (SEQ. ID NO. 411) | 5' AGT TCC GGT CAT GGC TAG G 3' (SEQ. ID NO. 412) | 145 | CT | 55° C. |
| WMS494 | 5' ATT GAA CAG GAC ATC AGG G 3' (SEQ. ID NO. 413) | 5' TTC CTG TGT TCC TTC G 3' (SEQ. ID NO. 414) | 198 | CA | 60° C. |
| WMS495 | 5' GAG AGC CTC GCG AAA TAT AGG 3' (SEQ. ID NO. 415) | 5' TGC TTC TGG TGG TGA TAT AC 3' (SEQ. ID NO. 416) | 168 | GA | 60° C. |
| WMS497 | 5' GTA GTG AAG ACA AGG GCA TT 3' (SEQ. ID NO. 417) | 5' CCG AAA GTT GGG TGA CAT AA 3' (SEQ. ID NO. 418) | >106 | GTimp | 55° C. |
| WMS499 | 5' ACT TGT ATG CTC CAT TGA TTG G 3' (SEQ. ID NO. 419) | 5' GGG GAG TGG AAA CTG CAT AG 3' (SEQ. ID NO. 420) | 145 | GA | 60° C. |
| WMS501 | 5' GGC TAT CTC TGG CGC TAA AA 3' (SEQ. ID NO. 421) | 5' TCC ACA AAC AAG TAG CGC C 3' (SEQ. ID NO. 422) | 172 | CA | 60° C. |
| WMS512 | 5' AGC CAC CAT CAG CAA AAA TT 3' (SEQ. ID NO. 423) | 5' GAA CAT GAG CAG TTT GGC AC 3' (SEQ. ID NO. 424) | 185 | CT | 60° C. |
| WMS513 | 5' ATC CGT AGC ACC TAC TGG TCA 3' (SEQ. ID NO. 425) | 5' GGT CTG TTC ATG CCA CAT TG 3' (SEQ. ID NO. 426) | 144 | CA | 60° C. |
| WMS515 | 5' AAC ACA ATG GCA AAT GCA GA 3' (SEQ. ID NO. 427) | 5' CCT TCC TAG TAA GTG TGC CTC A 3' (SEQ. ID NO. 428) | 134 | GTimp | 60° C. |
| WMS518 | 5' AAT CAC AAC AAG GCG TGA CA 3' (SEQ. ID NO. 429) | 5' CAG GGT GGT GCA TGC AT 3' (SEQ. ID NO. 430) | 166 | CA | 60° C. |
| WMS530 | 5' AAA TAG GAC AAC CCA CGG C 3' (SEQ. ID NO. 431) | 5' TCA ACT TCT TGG CCT CCA TC 3' (SEQ. ID NO. 432) | 186 | CT | 55° C. |
| WMS532 | 5' ACT GCG TGT GCC TAC AAT TG 3' (SEQ. ID NO. 433) | 5' TCA CTC GCA CTC GAT AGG C 3' (SEQ. ID NO. 434) | 142 | GT | 60° C. |
| WMS533 | 5' AAG GCG AAT CAA ACG GAA TA 3' (SEQ. ID NO. 435) | 5' GTT GCT TTA GGG GAA AAG CC 3' (SEQ. ID NO. 436) | 147 | CT,CA | 60° C. |

-continued

| WMS Number | WMS Primer Left | WMS Primer Right | Length (bp) in "cs" | Repeat Type | Annealing Temperature |
|---|---|---|---|---|---|
| WMS537 | 5' ACA TAA TGC TTC CTG TGC ACC 3' (SEQ. ID NO. 437) | 5' GCC ACT TTT GTG TCG TTC CT 3' (SEQ. ID NO. 438) | 209 | CA,TA | 60° C. |
| WMS538 | 5' GCA TTT CGG GTG AAC CC 3' (SEQ. ID NO. 439) | 5' GTT GCA TGT ATA CGT TAA GCG G 3' (SEQ. ID NO. 440) | 147 | GTimp | 60° C. |
| WMS540 | 5' TCT CGC TGT GAA ATC CTA TTT C 3' (SEQ. ID NO. 441) | 5' AGG CAT GGA TAG AGG GGC 3' (SEQ. ID NO. 442) | 129 | CTimp | 55° C. |
| WMS544 | 5' TAG AAT TCT TTA TGG GCT CTG C 3' (SEQ. ID NO. 443) | 5' AGG ATT CCA ATC CTT CAA AAT T 3' (SEQ. ID NO. 444) | 167 | CT,ATCT,CT | 55° C. |
| WMS550 | 5' CCC ACA AGA ACC TTT GAA GA 3' (SEQ. ID NO. 445) | 5' CAT TGT GTG TGC AAG GCA C 3' (SEQ. ID NO. 446) | 150 | CT,GT | 55° C. |
| WMS554 | 5' TGC CCA CAA CGG AAC TTG 3' (SEQ. ID NO. 447) | 5' GCA ACC ACC AAG CAC AAA GT 3' (SEQ. ID NO. 448) | 160 | CT,GTimp | 60° C. |
| WMS565 | 5' GCG TCA GAT ATG CCT ACC TAG G 3' (SEQ. ID NO. 449) | 5' AGT GAG TTA GCC CTG AGC CA 3' (SEQ. ID NO. 450) | 142 | CA | 60° C. |
| WMS566 | 5' TCT GTC TAC CCA TGG GAT TTG 3' (SEQ. ID NO. 451) | 5' CTG GCT TCG AGG TAA GCA AC 3' (SEQ. ID NO. 452) | 130 | CA,TA | 60° C. |
| WMS569 | 5' GGA AAC TTA TTG ATT GAA AT 3' (SEQ. ID NO. 453) | 5' TCA ATT TTG ACA GAA GAA TT 3' (SEQ. ID NO. 454) | 134 | GT | 47° C. |
| WMS570 | 5' TCG CCT TTT ACA GTC GGC 3' (SEQ. ID NO. 455) | 5' ATG GGT AGC TGA GAG CCA AA 3' (SEQ. ID NO. 456) | 143 | CT,GT | 60° C. |
| WMS573 | 5' AAG AGA TAA CAT GCA AGA AA 3' (SEQ. ID NO. 457) | 5' TTC AAA TAT GGA GAG ACT AC 3' (SEQ. ID NO. 458) | 212 | CA | 50° C. |
| WMS577 | 5' ATG GCA TAA TTT GGT GAA ATT G 3' (SEQ. ID NO. 459) | 5' TGT TTC AAG CCC AAC TTC TAT T 3' (SEQ. ID NO. 460) | 133 | CA,TA | 55° C. |
| WMS582 | 5' AAG CAC TAC GAA AAT ATG AC 3' (SEQ. ID NO. 461) | 5' TCT TAA GGG GTG TTA TCA TA 3' (SEQ. ID NO. 462) | 151 | CA | 50° C. |
| WMS583 | 5' TTC ACA CCC AAC CAA TAG CA 3' (SEQ. ID NO. 463) | 5' TCT AGG CAG ACA CAT GCC TG 3' (SEQ. ID NO. 464) | 165 | CA | 60° C. |
| WMS588 | 5' GAT CCC CAA TTG CAT GTT G 3' (SEQ. ID NO. 465) | 5' CTT GCA ACT GGG GGA CAC 3' (SEQ. ID NO. 466) | 102 | GT | 60° C. |

*'CS' Weizensoric 'Chinese Spring'

These markers are distinguished by a high degree of polymorphism between different wheat varieties or lines and usually detect several alleles per genetic locus in different wheat lines.

They can therefore be used for DNA fingerprinting, species identification, relationship or similarity studies, characterization of cytological lines, such as deletion lines, substitution lines, addition lines, etc. and all forms of genetic mappings, including mapping of individual genes and quantitative distinguishing features (QTLs). In addition, their use is also very suitable for automation and it is possible to carry out the detection of the products with nonradioactive methods.

With the help of this inventive marker, the possibility is provided, for example, of differentiating almost all European wheat lines.

The invention is described in greater detail below by means of examples.

1. Amplification of the Microsatellite Markers

The microsatellite markers are amplified according to the following protocol:
- 10 mM tris-HCl, pH 8
- 50 mM KCl
- 1.5 mM MgCl$_2$ (in a few exceptional cases 3 mM MgCl$_2$)
- 0.01% (w/v) gelatin
- 0.2 mM of each desoxynucleotide
- 250 nM of each primer (in each case to the left and right of a pair)
- 1-2 units taq polymerase
- 50-150 ng matrixes (template) DNA are amplified in a volume of 25 or 50 µL according to the following profile:

| | | |
|---|---|---|
| 92° C. | 3 minute | |
| 92° C. | 1 minute (denaturing phase) | |
| 60° C. | 1 minutes (annealing phase) | 45 cycles |
| 72° C. | 2 minutes (elongation phase) | |
| 72° C. | 10 minutes (extension phase) | |

The amplification takes place in a Perkin Elmer 9600 with lid heating or in an MJ Research Thermocycler without lid heating. In this apparatus, a layer of mineral oil is placed over the reactions. The temperature of the annealing phase depends on the melting point ($T_m$) of the primer and in some cases even is 50° C. or 55° C.

2. Separation of the Microsatellite Markers on Polyacrylamide Gels, Which Are Not Denaturing The PCR reactions are mixed with 1/10 volume of stop buffer (0.02 M tris acetate of pH 8.1, 0.025 M sodium acetate, 0.02 M EDTA, 70% glycerin, 0.2% SDS, 0.6% bromphenol blue, 0.6% xylene cyanol) and in each case 25 µL are separated in 10% polyacrylamide gels (1.5 mm thick, 18 cm long).

Formulation for polyacrylamide gel (10%):

| | |
|---|---|
| 25 mL | stock acrylamide solution (19 g acrylamide, 1 g bisacrylamide, diluted to 100 mL with water) |
| 10 mL | 5X TBE (1X TBE = 0.09 M tris borate of pH 8.3, 0.002 M EDTA |
| 15 mL | water | are mixed and the polymerization is started by the addition of 220 µL of ammonium persulfate (10%, freshly prepared) and 20 µL of TEMED. Immediately after the addition, the mixture is poured into the sealed gel mold and the comb for forming pockets is inserted. The polymerization is completed after about 1 hour. The gel is placed in the gel chamber and a preliminary run is carried out without samples for about 30 minutes at 150 volts in 1× TBE. After that, the samples are loaded (25 µL of each) and the separation is carried out for 14-16 hours at 100 volts.

After the electrophoresis is completed, the gel is stained for about minutes in ethidium bromide (1-2 drops of 10 mg/mL in 1 liter of water) and the fragments are made visible by a UV transilluminator and documented.

3. Separation of Microsatellite Markers on Denaturing Gels

For the separation of the amplified fragments on denaturing gels, an automatic laser fluorescence (A.L.F.) sequencer (Pharmacia), for example, is used. In order to enable the fragments to be detected by means of a laser, one primer per pair is marked at the 5' end with fluorescein. Per PCR reaction, 0.3 to 1.5 microliters are mixed with 2.5 microliters of stop buffer (deionized formamide; 5 mg/mL dextran blue), denatured (1 minute; 90° C.) and loaded onto the gel. Gel plates with a 9 cm separation distance are used, as recommended by the manufacturer for the fragment analysis. The gel solution contains 6.5% Long-Ranger (AT Biochem), 7M urea and 1.2× TBE buffer. The gels are 0.35 or 0.5 mm thick. The conditions for the gel run are 600 V, 40 mA, 50 W, 0.84 s data collection interval and 2 mW laser energy. The gel runs are ended after about 80 to 90 minutes. This is sufficient for detecting fragments up to a size of 300 bp. A gel can be used for four or five runs. For each gel run, a data set is obtained. With this data set and by means of internal size standards, the exact fragment sizes are determined in the computer program Fragment Manager (Pharmacia) and thus the smallest size differences of a base pair are determined.

The invention claimed is:

1. A method of genotyping plants of the species *Triticum aestivum* and the genus *Triticeae* at a microsatellite locus, the method comprising a) amplifying chromosomal DNA with one or more oligonucleotide primer pairs specifically hybridizing to said locus of a region of said chromosomal DNA, wherein said region of the DNA comprises a repeated motif to obtain an amplification product, b) wherein each primer pair consists of a first oligonucleotide of SEQ ID NO. x and a second oligonucleotide of SEQ ID NO. x+1, and wherein x=1, 3, 5, 7, 9, 11, 13, 15, 17, and/or 19; and c) size fractionating the amplification product to provide a measure of the said motif of the chromosomal DNA between said primer pairs, wherein the size of the amplification product is polymorphic for said locus and provides a marker for genotyping said plants.

2. The method of claim 1, further comprising the step of using the resulting genotype for a further step chosen from the group consisting of DNA fingerprinting, species identification, relationship studies, similarity studies, characterization of cytological lines, and genetic mapping.

3. The method claim 1, further comprising amplifying the chromosomal DNA with one or more primer pairs, wherein said primer pairs have a first oligonucleotide of SEQ ID NO: x and a second oligonucleotide of SEQ ID NO: x+1, and wherein x=95, 111, 156, 293, 337, 369, 437, 493, 553, and/or 557.

* * * * *

SEQUENCE LISTING

<160> NUMBER OF SEQ ID NOS: 466

<210> SEQ ID NO 1
<211> LENGTH: 20
<212> TYPE: DNA
<213> ORGANISM: Triticum sp.

<400> SEQUENCE: 1
ctatgaggcg gaggttgaag                                            20

```
<210> SEQ ID NO 2
<211> LENGTH: 18
<212> TYPE: DNA
<213> ORGANISM: Triticum sp.

<400> SEQUENCE: 2
tgcggtgctc ttccattt                                                 18

<210> SEQ ID NO 3
<211> LENGTH: 21
<212> TYPE: DNA
<213> ORGANISM: Triticum sp.

<400> SEQUENCE: 3
gcatctggta cactagctgc c                                             21

<210> SEQ ID NO 4
<211> LENGTH: 20
<212> TYPE: DNA
<213> ORGANISM: Triticum sp.

<400> SEQUENCE: 4
tcatggatgc atcacatcct                                               20

<210> SEQ ID NO 5
<211> LENGTH: 21
<212> TYPE: DNA
<213> ORGANISM: Triticum sp.

<400> SEQUENCE: 5
tcgattctga aaggttcatc g                                             21

<210> SEQ ID NO 6
<211> LENGTH: 21
<212> TYPE: DNA
<213> ORGANISM: Triticum sp.

<400> SEQUENCE: 6
cgatcaagta gttgaaagcg c                                             21

<210> SEQ ID NO 7
<211> LENGTH: 21
<212> TYPE: DNA
<213> ORGANISM: Triticum sp.

<400> SEQUENCE: 7
tctgatcccg tgagtgtaac a                                             21

<210> SEQ ID NO 8
<211> LENGTH: 22
<212> TYPE: DNA
<213> ORGANISM: Triticum sp.

<400> SEQUENCE: 8
gaaaaaaatt gcatatgagc cc                                            22

<210> SEQ ID NO 9
<211> LENGTH: 19
<212> TYPE: DNA
<213> ORGANISM: Triticum sp.

<400> SEQUENCE: 9
tgtcctacac ggaccacgt                                                19
```

```
<210> SEQ ID NO 10
<211> LENGTH: 19
<212> TYPE: DNA
<213> ORGANISM: Triticum sp.

<400> SEQUENCE: 10
gcattgacag atgcacacg                                                19

<210> SEQ ID NO 11
<211> LENGTH: 18
<212> TYPE: DNA
<213> ORGANISM: Triticum sp.

<400> SEQUENCE: 11
tcgacctgat cgcccta                                                  18

<210> SEQ ID NO 12
<211> LENGTH: 20
<212> TYPE: DNA
<213> ORGANISM: Triticum sp.

<400> SEQUENCE: 12
cgccctgggt gatgaatagt                                               20

<210> SEQ ID NO 13
<211> LENGTH: 21
<212> TYPE: DNA
<213> ORGANISM: Triticum sp.

<400> SEQUENCE: 13
accacacaaa caaggtaagc g                                             21

<210> SEQ ID NO 14
<211> LENGTH: 22
<212> TYPE: DNA
<213> ORGANISM: Triticum sp.

<400> SEQUENCE: 14
caaccctctt aattttgttg gg                                            22

<210> SEQ ID NO 15
<211> LENGTH: 19
<212> TYPE: DNA
<213> ORGANISM: Triticum sp.

<400> SEQUENCE: 15
aggccagaat ctgggaatg                                                19

<210> SEQ ID NO 16
<211> LENGTH: 20
<212> TYPE: DNA
<213> ORGANISM: Triticum sp.

<400> SEQUENCE: 16
ctccctagat gggagaaggg                                               20

<210> SEQ ID NO 17
<211> LENGTH: 20
<212> TYPE: DNA
<213> ORGANISM: Triticum sp.

<400> SEQUENCE: 17
agtggctggg agagtgtcat                                               20
```

<210> SEQ ID NO 18
<211> LENGTH: 18
<212> TYPE: DNA
<213> ORGANISM: Triticum sp.

<400> SEQUENCE: 18
gcccattacc gaggacac                                              18

<210> SEQ ID NO 19
<211> LENGTH: 18
<212> TYPE: DNA
<213> ORGANISM: Triticum sp.

<400> SEQUENCE: 19
ggcagagcag cgagactc                                              18

<210> SEQ ID NO 20
<211> LENGTH: 22
<212> TYPE: DNA
<213> ORGANISM: Triticum sp.

<400> SEQUENCE: 20
caagtggagc attaggtaca cg                                         22

<210> SEQ ID NO 21
<211> LENGTH: 20
<212> TYPE: DNA
<213> ORGANISM: Triticum sp.

<400> SEQUENCE: 21
acaaaggtaa gcagcacctg                                            20

<210> SEQ ID NO 22
<211> LENGTH: 18
<212> TYPE: DNA
<213> ORGANISM: Triticum sp.

<400> SEQUENCE: 22
accctcttgc ccgtgttg                                              18

<210> SEQ ID NO 23
<211> LENGTH: 20
<212> TYPE: DNA
<213> ORGANISM: Triticum sp.

<400> SEQUENCE: 23
acgttagaag gtgcaatggg                                            20

<210> SEQ ID NO 24
<211> LENGTH: 19
<212> TYPE: DNA
<213> ORGANISM: Triticum sp.

<400> SEQUENCE: 24
agtggatgca ccgactttg                                             19

<210> SEQ ID NO 25
<211> LENGTH: 20
<212> TYPE: DNA
<213> ORGANISM: Triticum sp.

<400> SEQUENCE: 25

```
cactacaact atgcgctcgc                                              20
```

```
<210> SEQ ID NO 26
<211> LENGTH: 20
<212> TYPE: DNA
<213> ORGANISM: Triticum sp.

<400> SEQUENCE: 26
tccattggct tctctctcaa                                              20

<210> SEQ ID NO 27
<211> LENGTH: 20
<212> TYPE: DNA
<213> ORGANISM: Triticum sp.

<400> SEQUENCE: 27
gatcaaacac acacccctcc                                              20

<210> SEQ ID NO 28
<211> LENGTH: 20
<212> TYPE: DNA
<213> ORGANISM: Triticum sp.

<400> SEQUENCE: 28
aatgcaaagt gaaaaacccg                                              20

<210> SEQ ID NO 29
<211> LENGTH: 21
<212> TYPE: DNA
<213> ORGANISM: Triticum sp.

<400> SEQUENCE: 29
aagatggacg tatgcatcac a                                            21

<210> SEQ ID NO 30
<211> LENGTH: 20
<212> TYPE: DNA
<213> ORGANISM: Triticum sp.

<400> SEQUENCE: 30
gccatatttg atgacgcata                                              20

<210> SEQ ID NO 31
<211> LENGTH: 18
<212> TYPE: DNA
<213> ORGANISM: Triticum sp.

<400> SEQUENCE: 31
tctcccatcc aacgcctc                                                18

<210> SEQ ID NO 32
<211> LENGTH: 20
<212> TYPE: DNA
<213> ORGANISM: Triticum sp.

<400> SEQUENCE: 32
tgttggtggc ttgactattg                                              20

<210> SEQ ID NO 33
<211> LENGTH: 20
<212> TYPE: DNA
<213> ORGANISM: Triticum sp.

<400> SEQUENCE: 33
```

```
ctgttcttgc gtggcattaa                                                20

<210> SEQ ID NO 34
<211> LENGTH: 22
<212> TYPE: DNA
<213> ORGANISM: Triticum sp.

<400> SEQUENCE: 34
aataaggaca caattgggat gg                                             22

<210> SEQ ID NO 35
<211> LENGTH: 21
<212> TYPE: DNA
<213> ORGANISM: Triticum sp.

<400> SEQUENCE: 35
attaatacct gagggaggtg c                                              21

<210> SEQ ID NO 36
<211> LENGTH: 20
<212> TYPE: DNA
<213> ORGANISM: Triticum sp.

<400> SEQUENCE: 36
ggtctcagga gcaagaacac                                                20

<210> SEQ ID NO 37
<211> LENGTH: 20
<212> TYPE: DNA
<213> ORGANISM: Triticum sp.

<400> SEQUENCE: 37
cgacaatggg gtcttagcat                                                20

<210> SEQ ID NO 38
<211> LENGTH: 22
<212> TYPE: DNA
<213> ORGANISM: Triticum sp.

<400> SEQUENCE: 38
tgcacactta aattacatcc gc                                             22

<210> SEQ ID NO 39
<211> LENGTH: 21
<212> TYPE: DNA
<213> ORGANISM: Triticum sp.

<400> SEQUENCE: 39
tctgtaggct ctctccgact g                                              21

<210> SEQ ID NO 40
<211> LENGTH: 20
<212> TYPE: DNA
<213> ORGANISM: Triticum sp.

<400> SEQUENCE: 40
acctgatcag atcccactcg                                                20

<210> SEQ ID NO 41
<211> LENGTH: 19
<212> TYPE: DNA
<213> ORGANISM: Triticum sp.
```

```
<400> SEQUENCE: 41
ctaaacacga cagcggtgg                                             19

<210> SEQ ID NO 42
<211> LENGTH: 20
<212> TYPE: DNA
<213> ORGANISM: Triticum sp.

<400> SEQUENCE: 42
gatatgtgag cagcggtcag                                            20

<210> SEQ ID NO 43
<211> LENGTH: 22
<212> TYPE: DNA
<213> ORGANISM: Triticum sp.

<400> SEQUENCE: 43
attcgaggtt aggaggaaga gg                                         22

<210> SEQ ID NO 44
<211> LENGTH: 20
<212> TYPE: DNA
<213> ORGANISM: Triticum sp.

<400> SEQUENCE: 44
gagggtcggc ctataagacc                                            20

<210> SEQ ID NO 45
<211> LENGTH: 22
<212> TYPE: DNA
<213> ORGANISM: Triticum sp.

<400> SEQUENCE: 45
acaaacagaa aatcaaaacc cg                                         22

<210> SEQ ID NO 46
<211> LENGTH: 19
<212> TYPE: DNA
<213> ORGANISM: Triticum sp.

<400> SEQUENCE: 46
atccatcgcc attggagtg                                             19

<210> SEQ ID NO 47
<211> LENGTH: 20
<212> TYPE: DNA
<213> ORGANISM: Triticum sp.

<400> SEQUENCE: 47
gatgttgcca cttgagcatg                                            20

<210> SEQ ID NO 48
<211> LENGTH: 22
<212> TYPE: DNA
<213> ORGANISM: Triticum sp.

<400> SEQUENCE: 48
gattagtcaa atggaacacc cc                                         22

<210> SEQ ID NO 49
<211> LENGTH: 22
<212> TYPE: DNA
<213> ORGANISM: Triticum sp.
```

```
<400> SEQUENCE: 49
tgactaacat cctttgtcac gc                                    22

<210> SEQ ID NO 50
<211> LENGTH: 20
<212> TYPE: DNA
<213> ORGANISM: Triticum sp.

<400> SEQUENCE: 50
catgtctcaa ccacccacag                                       20

<210> SEQ ID NO 51
<211> LENGTH: 20
<212> TYPE: DNA
<213> ORGANISM: Triticum sp.

<400> SEQUENCE: 51
gatccacctt cctctctctc                                       20

<210> SEQ ID NO 52
<211> LENGTH: 20
<212> TYPE: DNA
<213> ORGANISM: Triticum sp.

<400> SEQUENCE: 52
gattatactg gtgccgaaac                                       20

<210> SEQ ID NO 53
<211> LENGTH: 20
<212> TYPE: DNA
<213> ORGANISM: Triticum sp.

<400> SEQUENCE: 53
tcctctacaa acaaacacac                                       20

<210> SEQ ID NO 54
<211> LENGTH: 20
<212> TYPE: DNA
<213> ORGANISM: Triticum sp.

<400> SEQUENCE: 54
ctcgcaacta gaggtgtatg                                       20

<210> SEQ ID NO 55
<211> LENGTH: 19
<212> TYPE: DNA
<213> ORGANISM: Triticum sp.

<400> SEQUENCE: 55
gggtgggaga aaggagatg                                        19

<210> SEQ ID NO 56
<211> LENGTH: 19
<212> TYPE: DNA
<213> ORGANISM: Triticum sp.

<400> SEQUENCE: 56
aaaccatcct ccatcctgg                                        19

<210> SEQ ID NO 57
<211> LENGTH: 18
<212> TYPE: DNA
```

<213> ORGANISM: Triticum sp.

<400> SEQUENCE: 57
gccatggcta tcacccag                                                18

<210> SEQ ID NO 58
<211> LENGTH: 20
<212> TYPE: DNA
<213> ORGANISM: Triticum sp.

<400> SEQUENCE: 58
actgttcggt gcaatttgag                                              20

<210> SEQ ID NO 59
<211> LENGTH: 18
<212> TYPE: DNA
<213> ORGANISM: Triticum sp.

<400> SEQUENCE: 59
cacacgctcc accatgac                                                18

<210> SEQ ID NO 60
<211> LENGTH: 19
<212> TYPE: DNA
<213> ORGANISM: Triticum sp.

<400> SEQUENCE: 60
gttgagttga tgcgggagg                                               19

<210> SEQ ID NO 61
<211> LENGTH: 20
<212> TYPE: DNA
<213> ORGANISM: Triticum sp.

<400> SEQUENCE: 61
agcacatttt aacacagata                                              20

<210> SEQ ID NO 62
<211> LENGTH: 20
<212> TYPE: DNA
<213> ORGANISM: Triticum sp.

<400> SEQUENCE: 62
atctgtgaaa ttttgaaaac                                              20

<210> SEQ ID NO 63
<211> LENGTH: 20
<212> TYPE: DNA
<213> ORGANISM: Triticum sp.

<400> SEQUENCE: 63
tcagtgggca agctacacag                                              20

<210> SEQ ID NO 64
<211> LENGTH: 18
<212> TYPE: DNA
<213> ORGANISM: Triticum sp.

<400> SEQUENCE: 64
aaaacttagt agccgcgt                                                18

<210> SEQ ID NO 65
<211> LENGTH: 20

-continued

```
<212> TYPE: DNA
<213> ORGANISM: Triticum sp.

<400> SEQUENCE: 65
agctctgctt cacgaggaag                                                 20

<210> SEQ ID NO 66
<211> LENGTH: 21
<212> TYPE: DNA
<213> ORGANISM: Triticum sp.

<400> SEQUENCE: 66
ctcctcttta tatcgcgtcc c                                               21

<210> SEQ ID NO 67
<211> LENGTH: 20
<212> TYPE: DNA
<213> ORGANISM: Triticum sp.

<400> SEQUENCE: 67
aatccccacc gattcttctc                                                 20

<210> SEQ ID NO 68
<211> LENGTH: 20
<212> TYPE: DNA
<213> ORGANISM: Triticum sp.

<400> SEQUENCE: 68
agttcgtggg tctctgatgg                                                 20

<210> SEQ ID NO 69
<211> LENGTH: 22
<212> TYPE: DNA
<213> ORGANISM: Triticum sp.

<400> SEQUENCE: 69
taccaaatcg aaacacatca gg                                              22

<210> SEQ ID NO 70
<211> LENGTH: 21
<212> TYPE: DNA
<213> ORGANISM: Triticum sp.

<400> SEQUENCE: 70
catatcaagg tctccttccc c                                               21

<210> SEQ ID NO 71
<211> LENGTH: 20
<212> TYPE: DNA
<213> ORGANISM: Triticum sp.

<400> SEQUENCE: 71
atctaaacaa gacggcggtg                                                 20

<210> SEQ ID NO 72
<211> LENGTH: 20
<212> TYPE: DNA
<213> ORGANISM: Triticum sp.

<400> SEQUENCE: 72
atctgtgaca accggtgaga                                                 20

<210> SEQ ID NO 73
```

-continued

```
<211> LENGTH: 21
<212> TYPE: DNA
<213> ORGANISM: Triticum sp.

<400> SEQUENCE: 73
catggaactt agacagaatt g                                              21

<210> SEQ ID NO 74
<211> LENGTH: 21
<212> TYPE: DNA
<213> ORGANISM: Triticum sp.

<400> SEQUENCE: 74
cagtacttgg tactgaacag g                                              21

<210> SEQ ID NO 75
<211> LENGTH: 22
<212> TYPE: DNA
<213> ORGANISM: Triticum sp.

<400> SEQUENCE: 75
tgtcaacatc gttttgaaaa gg                                             22

<210> SEQ ID NO 76
<211> LENGTH: 20
<212> TYPE: DNA
<213> ORGANISM: Triticum sp.

<400> SEQUENCE: 76
acactgtcaa cctggcaatg                                                20

<210> SEQ ID NO 77
<211> LENGTH: 19
<212> TYPE: DNA
<213> ORGANISM: Triticum sp.

<400> SEQUENCE: 77
gacagcacct tgcccttttg                                                19

<210> SEQ ID NO 78
<211> LENGTH: 19
<212> TYPE: DNA
<213> ORGANISM: Triticum sp.

<400> SEQUENCE: 78
catcggcaac atgctcatc                                                 19

<210> SEQ ID NO 79
<211> LENGTH: 22
<212> TYPE: DNA
<213> ORGANISM: Triticum sp.

<400> SEQUENCE: 79
atggagatat ttggcctaca ac                                             22

<210> SEQ ID NO 80
<211> LENGTH: 20
<212> TYPE: DNA
<213> ORGANISM: Triticum sp.

<400> SEQUENCE: 80
cttgacttca aggcgtgaca                                                20
```

```
<210> SEQ ID NO 81
<211> LENGTH: 22
<212> TYPE: DNA
<213> ORGANISM: Triticum sp.

<400> SEQUENCE: 81
tttgctgtgg tacgaaacat ac                                              22

<210> SEQ ID NO 82
<211> LENGTH: 22
<212> TYPE: DNA
<213> ORGANISM: Triticum sp.

<400> SEQUENCE: 82
actcacaaat gtctaataaa ac                                              22

<210> SEQ ID NO 83
<211> LENGTH: 20
<212> TYPE: DNA
<213> ORGANISM: Triticum sp.

<400> SEQUENCE: 83
ccaaaaaaac tgcctgcatg                                                 20

<210> SEQ ID NO 84
<211> LENGTH: 19
<212> TYPE: DNA
<213> ORGANISM: Triticum sp.

<400> SEQUENCE: 84
ctctggcatt gctccttgg                                                  19

<210> SEQ ID NO 85
<211> LENGTH: 20
<212> TYPE: DNA
<213> ORGANISM: Triticum sp.

<400> SEQUENCE: 85
gtgaggcagc aagagagaaa                                                 20

<210> SEQ ID NO 86
<211> LENGTH: 21
<212> TYPE: DNA
<213> ORGANISM: Triticum sp.

<400> SEQUENCE: 86
caaagcttga ctcagaccaa a                                               21

<210> SEQ ID NO 87
<211> LENGTH: 21
<212> TYPE: DNA
<213> ORGANISM: Triticum sp.

<400> SEQUENCE: 87
cattgttttc tgcctctagc c                                               21

<210> SEQ ID NO 88
<211> LENGTH: 21
<212> TYPE: DNA
<213> ORGANISM: Triticum sp.

<400> SEQUENCE: 88
ctagcatcga acctgaacaa g                                               21
```

```
<210> SEQ ID NO 89
<211> LENGTH: 20
<212> TYPE: DNA
<213> ORGANISM: Triticum sp.

<400> SEQUENCE: 89
gatctcgtca cccggaattc                                               20

<210> SEQ ID NO 90
<211> LENGTH: 20
<212> TYPE: DNA
<213> ORGANISM: Triticum sp.

<400> SEQUENCE: 90
tggtagagaa ggacggagag                                               20

<210> SEQ ID NO 91
<211> LENGTH: 20
<212> TYPE: DNA
<213> ORGANISM: Triticum sp.

<400> SEQUENCE: 91
tcacagagag agagggaggg                                               20

<210> SEQ ID NO 92
<211> LENGTH: 20
<212> TYPE: DNA
<213> ORGANISM: Triticum sp.

<400> SEQUENCE: 92
atgtgtacat gttgcctgca                                               20

<210> SEQ ID NO 93
<211> LENGTH: 18
<212> TYPE: DNA
<213> ORGANISM: Triticum sp.

<400> SEQUENCE: 93
caatcatttc cccctccc                                                 18

<210> SEQ ID NO 94
<211> LENGTH: 22
<212> TYPE: DNA
<213> ORGANISM: Triticum sp.

<400> SEQUENCE: 94
aatcattgga aatccatatg cc                                            22

<210> SEQ ID NO 95
<211> LENGTH: 22
<212> TYPE: DNA
<213> ORGANISM: Triticum sp.

<400> SEQUENCE: 95
ccaaccgtgc tattagtcat tc                                            22

<210> SEQ ID NO 96
<211> LENGTH: 19
<212> TYPE: DNA
<213> ORGANISM: Triticum sp.

<400> SEQUENCE: 96
caatgcaggc cctcctaac                                                19
```

```
<210> SEQ ID NO 97
<211> LENGTH: 18
<212> TYPE: DNA
<213> ORGANISM: Triticum sp.

<400> SEQUENCE: 97
gtcgtcgcgg taagcttg                                                 18

<210> SEQ ID NO 98
<211> LENGTH: 20
<212> TYPE: DNA
<213> ORGANISM: Triticum sp.

<400> SEQUENCE: 98
gagtgaacac acgaggcttg                                               20

<210> SEQ ID NO 99
<211> LENGTH: 18
<212> TYPE: DNA
<213> ORGANISM: Triticum sp.

<400> SEQUENCE: 99
gggccaacac tggaacac                                                 18

<210> SEQ ID NO 100
<211> LENGTH: 20
<212> TYPE: DNA
<213> ORGANISM: Triticum sp.

<400> SEQUENCE: 100
gcagaagctt gttggtaggc                                               20

<210> SEQ ID NO 101
<211> LENGTH: 21
<212> TYPE: DNA
<213> ORGANISM: Triticum sp.

<400> SEQUENCE: 101
ttcaattcag tcttggcttg g                                             21

<210> SEQ ID NO 102
<211> LENGTH: 22
<212> TYPE: DNA
<213> ORGANISM: Triticum sp.

<400> SEQUENCE: 102
ctgcaggaaa aaagtacac cc                                             22

<210> SEQ ID NO 103
<211> LENGTH: 20
<212> TYPE: DNA
<213> ORGANISM: Triticum sp.

<400> SEQUENCE: 103
gatcgagtga tggcagatgg                                               20

<210> SEQ ID NO 104
<211> LENGTH: 20
<212> TYPE: DNA
<213> ORGANISM: Triticum sp.

<400> SEQUENCE: 104
```

```
tgtgaattac ttggacgtgg                                              20

<210> SEQ ID NO 105
<211> LENGTH: 20
<212> TYPE: DNA
<213> ORGANISM: Triticum sp.

<400> SEQUENCE: 105
agtggatcga caaggctctg                                              20

<210> SEQ ID NO 106
<211> LENGTH: 20
<212> TYPE: DNA
<213> ORGANISM: Triticum sp.

<400> SEQUENCE: 106
agaagaagca aagccttccc                                              20

<210> SEQ ID NO 107
<211> LENGTH: 20
<212> TYPE: DNA
<213> ORGANISM: Triticum sp.

<400> SEQUENCE: 107
acctcgacag acctggtacg                                              20

<210> SEQ ID NO 108
<211> LENGTH: 20
<212> TYPE: DNA
<213> ORGANISM: Triticum sp.

<400> SEQUENCE: 108
gtctttgtca cccgatggac                                              20

<210> SEQ ID NO 109
<211> LENGTH: 19
<212> TYPE: DNA
<213> ORGANISM: Triticum sp.

<400> SEQUENCE: 109
acatttctcc cccatcgtc                                               19

<210> SEQ ID NO 110
<211> LENGTH: 20
<212> TYPE: DNA
<213> ORGANISM: Triticum sp.

<400> SEQUENCE: 110
ttgtaaacaa atcgcatgcg                                              20

<210> SEQ ID NO 111
<211> LENGTH: 20
<212> TYPE: DNA
<213> ORGANISM: Triticum sp.

<400> SEQUENCE: 111
tgcagtggtc agatgtttcc                                              20

<210> SEQ ID NO 112
<211> LENGTH: 20
<212> TYPE: DNA
<213> ORGANISM: Triticum sp.

<400> SEQUENCE: 112
```

```
cttttctttc agattgcgcc                                               20

<210> SEQ ID NO 113
<211> LENGTH: 22
<212> TYPE: DNA
<213> ORGANISM: Triticum sp.

<400> SEQUENCE: 113
accactgcag agaacacata cg                                            22

<210> SEQ ID NO 114
<211> LENGTH: 21
<212> TYPE: DNA
<213> ORGANISM: Triticum sp.

<400> SEQUENCE: 114
gtgctctgct ctaagtgtgg g                                             21

<210> SEQ ID NO 115
<211> LENGTH: 22
<212> TYPE: DNA
<213> ORGANISM: Triticum sp.

<400> SEQUENCE: 115
gggttcctat ctggtaaatc cc                                            22

<210> SEQ ID NO 116
<211> LENGTH: 20
<212> TYPE: DNA
<213> ORGANISM: Triticum sp.

<400> SEQUENCE: 116
gacacacatg ttcctgccac                                               20

<210> SEQ ID NO 117
<211> LENGTH: 20
<212> TYPE: DNA
<213> ORGANISM: Triticum sp.

<400> SEQUENCE: 117
aagttgagtt gatgcgggag                                               20

<210> SEQ ID NO 118
<211> LENGTH: 19
<212> TYPE: DNA
<213> ORGANISM: Triticum sp.

<400> SEQUENCE: 118
ccatgaccag catccactc                                                19

<210> SEQ ID NO 119
<211> LENGTH: 20
<212> TYPE: DNA
<213> ORGANISM: Triticum sp.

<400> SEQUENCE: 119
atccgcctaa ggaatagtgt                                               20

<210> SEQ ID NO 120
<211> LENGTH: 19
<212> TYPE: DNA
<213> ORGANISM: Triticum sp.
```

```
<400> SEQUENCE: 120
gatcgcacgg gagagagag                                                 19

<210> SEQ ID NO 121
<211> LENGTH: 20
<212> TYPE: DNA
<213> ORGANISM: Triticum sp.

<400> SEQUENCE: 121
tcattggtaa tgaggagaga                                                20

<210> SEQ ID NO 122
<211> LENGTH: 20
<212> TYPE: DNA
<213> ORGANISM: Triticum sp.

<400> SEQUENCE: 122
gaaccattca tgtgcatgtc                                                20

<210> SEQ ID NO 123
<211> LENGTH: 21
<212> TYPE: DNA
<213> ORGANISM: Triticum sp.

<400> SEQUENCE: 123
tgatgtagtg agcccatagg c                                              21

<210> SEQ ID NO 124
<211> LENGTH: 20
<212> TYPE: DNA
<213> ORGANISM: Triticum sp.

<400> SEQUENCE: 124
ttgcacacag ccaaataagg                                                20

<210> SEQ ID NO 125
<211> LENGTH: 20
<212> TYPE: DNA
<213> ORGANISM: Triticum sp.

<400> SEQUENCE: 125
gcagagcctg gttcaaaaag                                                20

<210> SEQ ID NO 126
<211> LENGTH: 20
<212> TYPE: DNA
<213> ORGANISM: Triticum sp.

<400> SEQUENCE: 126
cgcctctagc gagagctatg                                                20

<210> SEQ ID NO 127
<211> LENGTH: 18
<212> TYPE: DNA
<213> ORGANISM: Triticum sp.

<400> SEQUENCE: 127
aggagcagcg gaacgaac                                                  18

<210> SEQ ID NO 128
<211> LENGTH: 20
<212> TYPE: DNA
<213> ORGANISM: Triticum sp.
```

```
<400> SEQUENCE: 128
agaaatacgg aaacccaccc                                               20

<210> SEQ ID NO 129
<211> LENGTH: 21
<212> TYPE: DNA
<213> ORGANISM: Triticum sp.

<400> SEQUENCE: 129
gtgcttgctg agctatgagt c                                             21

<210> SEQ ID NO 130
<211> LENGTH: 19
<212> TYPE: DNA
<213> ORGANISM: Triticum sp.

<400> SEQUENCE: 130
gtgccacgtg gtacctttg                                                19

<210> SEQ ID NO 131
<211> LENGTH: 18
<212> TYPE: DNA
<213> ORGANISM: Triticum sp.

<400> SEQUENCE: 131
agactgttgt ttgcgggc                                                 18

<210> SEQ ID NO 132
<211> LENGTH: 22
<212> TYPE: DNA
<213> ORGANISM: Triticum sp.

<400> SEQUENCE: 132
tagcacgaca gttgtatgca tg                                            22

<210> SEQ ID NO 133
<211> LENGTH: 20
<212> TYPE: DNA
<213> ORGANISM: Triticum sp.

<400> SEQUENCE: 133
ggttttcttt cagattgcgc                                               20

<210> SEQ ID NO 134
<211> LENGTH: 21
<212> TYPE: DNA
<213> ORGANISM: Triticum sp.

<400> SEQUENCE: 134
cgttgtctaa tcttgccttg c                                             21

<210> SEQ ID NO 135
<211> LENGTH: 20
<212> TYPE: DNA
<213> ORGANISM: Triticum sp.

<400> SEQUENCE: 135
ctttgtgcac ctctctctcc                                               20

<210> SEQ ID NO 136
<211> LENGTH: 21
<212> TYPE: DNA
```

<213> ORGANISM: Triticum sp.

<400> SEQUENCE: 136
aattgtgttg atgatttggg g                                         21

<210> SEQ ID NO 137
<211> LENGTH: 20
<212> TYPE: DNA
<213> ORGANISM: Triticum sp.

<400> SEQUENCE: 137
gatctgctct actctcctcc                                           20

<210> SEQ ID NO 138
<211> LENGTH: 20
<212> TYPE: DNA
<213> ORGANISM: Triticum sp.

<400> SEQUENCE: 138
cgacgcagaa cttaaacaag                                           20

<210> SEQ ID NO 139
<211> LENGTH: 18
<212> TYPE: DNA
<213> ORGANISM: Triticum sp.

<400> SEQUENCE: 139
aggtgccgtc gcgtctac                                             18

<210> SEQ ID NO 140
<211> LENGTH: 18
<212> TYPE: DNA
<213> ORGANISM: Triticum sp.

<400> SEQUENCE: 140
accccccacg tcagagag                                             18

<210> SEQ ID NO 141
<211> LENGTH: 21
<212> TYPE: DNA
<213> ORGANISM: Triticum sp.

<400> SEQUENCE: 141
gagaaagagg tctggaggtc g                                         21

<210> SEQ ID NO 142
<211> LENGTH: 21
<212> TYPE: DNA
<213> ORGANISM: Triticum sp.

<400> SEQUENCE: 142
caaaatgcac aagaatggag g                                         21

<210> SEQ ID NO 143
<211> LENGTH: 20
<212> TYPE: DNA
<213> ORGANISM: Triticum sp.

<400> SEQUENCE: 143
ttgaaccgga aggagtacag                                           20

<210> SEQ ID NO 144
<211> LENGTH: 21

```
<212> TYPE: DNA
<213> ORGANISM: Triticum sp.

<400> SEQUENCE: 144
tcagtttatt tgggcatgt g                                          21

<210> SEQ ID NO 145
<211> LENGTH: 19
<212> TYPE: DNA
<213> ORGANISM: Triticum sp.

<400> SEQUENCE: 145
tcaacggaac agatgagcg                                            19

<210> SEQ ID NO 146
<211> LENGTH: 20
<212> TYPE: DNA
<213> ORGANISM: Triticum sp.

<400> SEQUENCE: 146
gacctgatga gagcaagcac                                           20

<210> SEQ ID NO 147
<211> LENGTH: 17
<212> TYPE: DNA
<213> ORGANISM: Triticum sp.

<400> SEQUENCE: 147
cccaaagcag cgcaagc                                              17

<210> SEQ ID NO 148
<211> LENGTH: 18
<212> TYPE: DNA
<213> ORGANISM: Triticum sp.

<400> SEQUENCE: 148
accaatgcta tcggctcg                                             18

<210> SEQ ID NO 149
<211> LENGTH: 18
<212> TYPE: DNA
<213> ORGANISM: Triticum sp.

<400> SEQUENCE: 149
cgacccggtt cacttcag                                             18

<210> SEQ ID NO 150
<211> LENGTH: 20
<212> TYPE: DNA
<213> ORGANISM: Triticum sp.

<400> SEQUENCE: 150
agtcgccgtt gtatagtgcc                                           20

<210> SEQ ID NO 151
<211> LENGTH: 22
<212> TYPE: DNA
<213> ORGANISM: Triticum sp.

<400> SEQUENCE: 151
tgcatcaaga atagtgtgga ag                                        22

<210> SEQ ID NO 152
```

```
<211> LENGTH: 20
<212> TYPE: DNA
<213> ORGANISM: Triticum sp.

<400> SEQUENCE: 152
tgagaggaag gctcacacct                                              20

<210> SEQ ID NO 153
<211> LENGTH: 20
<212> TYPE: DNA
<213> ORGANISM: Triticum sp.

<400> SEQUENCE: 153
aagcaacatt tgctgcaatg                                              20

<210> SEQ ID NO 154
<211> LENGTH: 22
<212> TYPE: DNA
<213> ORGANISM: Triticum sp.

<400> SEQUENCE: 154
tgcagttaac ttgttgaaag ga                                           22

<210> SEQ ID NO 155
<211> LENGTH: 20
<212> TYPE: DNA
<213> ORGANISM: Triticum sp.

<400> SEQUENCE: 155
tgcctggctc gttctatctc                                              20

<210> SEQ ID NO 156
<211> LENGTH: 20
<212> TYPE: DNA
<213> ORGANISM: Triticum sp.

<400> SEQUENCE: 156
ctagcttagc actgtcgccc                                              20

<210> SEQ ID NO 157
<211> LENGTH: 18
<212> TYPE: DNA
<213> ORGANISM: Triticum sp.

<400> SEQUENCE: 157
cggcaaacgg atatcgac                                                18

<210> SEQ ID NO 158
<211> LENGTH: 22
<212> TYPE: DNA
<213> ORGANISM: Triticum sp.

<400> SEQUENCE: 158
aacagtaact ctcgccatag cc                                           22

<210> SEQ ID NO 159
<211> LENGTH: 20
<212> TYPE: DNA
<213> ORGANISM: Triticum sp.

<400> SEQUENCE: 159
gatgagcgac acctagcctc                                              20
```

```
<210> SEQ ID NO 160
<211> LENGTH: 18
<212> TYPE: DNA
<213> ORGANISM: Triticum sp.

<400> SEQUENCE: 160
ggggtccgag tccacaac                                                 18

<210> SEQ ID NO 161
<211> LENGTH: 18
<212> TYPE: DNA
<213> ORGANISM: Triticum sp.

<400> SEQUENCE: 161
tgagtccagc actgctgc                                                 18

<210> SEQ ID NO 162
<211> LENGTH: 20
<212> TYPE: DNA
<213> ORGANISM: Triticum sp.

<400> SEQUENCE: 162
caacatccgc tcgtattcaa                                               20

<210> SEQ ID NO 163
<211> LENGTH: 22
<212> TYPE: DNA
<213> ORGANISM: Triticum sp.

<400> SEQUENCE: 163
tcatatgcac ctctttccta gg                                            22

<210> SEQ ID NO 164
<211> LENGTH: 19
<212> TYPE: DNA
<213> ORGANISM: Triticum sp.

<400> SEQUENCE: 164
gtgtgccacc tttgacgtc                                                19

<210> SEQ ID NO 165
<211> LENGTH: 18
<212> TYPE: DNA
<213> ORGANISM: Triticum sp.

<400> SEQUENCE: 165
agctcgggat gaagcgtg                                                 18

<210> SEQ ID NO 166
<211> LENGTH: 17
<212> TYPE: DNA
<213> ORGANISM: Triticum sp.

<400> SEQUENCE: 166
gatccgccgc tgcgttt                                                  17

<210> SEQ ID NO 167
<211> LENGTH: 17
<212> TYPE: DNA
<213> ORGANISM: Triticum sp.

<400> SEQUENCE: 167
atctcaacgg caagccg                                                  17
```

<210> SEQ ID NO 168
<211> LENGTH: 19
<212> TYPE: DNA
<213> ORGANISM: Triticum sp.

<400> SEQUENCE: 168
ctgatgcaag caatccacc                                              19

<210> SEQ ID NO 169
<211> LENGTH: 23
<212> TYPE: DNA
<213> ORGANISM: Triticum sp.

<400> SEQUENCE: 169
tcaaaacata aatgttcatt gga                                         23

<210> SEQ ID NO 170
<211> LENGTH: 22
<212> TYPE: DNA
<213> ORGANISM: Triticum sp.

<400> SEQUENCE: 170
tcaaccgtgt gtaattttgt cc                                          22

<210> SEQ ID NO 171
<211> LENGTH: 22
<212> TYPE: DNA
<213> ORGANISM: Triticum sp.

<400> SEQUENCE: 171
gagtcctgat gtgaagctgt tg                                          22

<210> SEQ ID NO 172
<211> LENGTH: 20
<212> TYPE: DNA
<213> ORGANISM: Triticum sp.

<400> SEQUENCE: 172
ctcattgggg tgtgtacgtg                                             20

<210> SEQ ID NO 173
<211> LENGTH: 22
<212> TYPE: DNA
<213> ORGANISM: Triticum sp.

<400> SEQUENCE: 173
gaatcacttg tgaagcatct gg                                          22

<210> SEQ ID NO 174
<211> LENGTH: 20
<212> TYPE: DNA
<213> ORGANISM: Triticum sp.

<400> SEQUENCE: 174
ctggatgcat cacatccaac                                             20

<210> SEQ ID NO 175
<211> LENGTH: 18
<212> TYPE: DNA
<213> ORGANISM: Triticum sp.

<400> SEQUENCE: 175
tcgcttctac cgctcacc                                               18

<210> SEQ ID NO 176
<211> LENGTH: 17
<212> TYPE: DNA
<213> ORGANISM: Triticum sp.

<400> SEQUENCE: 176
agtgccttgc cgaggtc                                                    17

<210> SEQ ID NO 177
<211> LENGTH: 20
<212> TYPE: DNA
<213> ORGANISM: Triticum sp.

<400> SEQUENCE: 177
tcttccaact aaagcatagc                                                 20

<210> SEQ ID NO 178
<211> LENGTH: 22
<212> TYPE: DNA
<213> ORGANISM: Triticum sp.

<400> SEQUENCE: 178
cttccatgga ctacatacta gc                                              22

<210> SEQ ID NO 179
<211> LENGTH: 18
<212> TYPE: DNA
<213> ORGANISM: Triticum sp.

<400> SEQUENCE: 179
tccaaggcag taggcagg                                                   18

<210> SEQ ID NO 180
<211> LENGTH: 20
<212> TYPE: DNA
<213> ORGANISM: Triticum sp.

<400> SEQUENCE: 180
tgttgttggc ctgtatgcat                                                 20

<210> SEQ ID NO 181
<211> LENGTH: 18
<212> TYPE: DNA
<213> ORGANISM: Triticum sp.

<400> SEQUENCE: 181
ggcagctgag gcaatctg                                                   18

<210> SEQ ID NO 182
<211> LENGTH: 18
<212> TYPE: DNA
<213> ORGANISM: Triticum sp.

<400> SEQUENCE: 182
tttggacatt tcccagcg                                                   18

<210> SEQ ID NO 183
<211> LENGTH: 17
<212> TYPE: DNA
<213> ORGANISM: Triticum sp.

<400> SEQUENCE: 183

```
cagcgcagtt agctcgc                                                    17

<210> SEQ ID NO 184
<211> LENGTH: 18
<212> TYPE: DNA
<213> ORGANISM: Triticum sp.

<400> SEQUENCE: 184
atctgtccat tcgagcgc                                                   18

<210> SEQ ID NO 185
<211> LENGTH: 21
<212> TYPE: DNA
<213> ORGANISM: Triticum sp.

<400> SEQUENCE: 185
gcaatctttt ttctgaccac g                                               21

<210> SEQ ID NO 186
<211> LENGTH: 17
<212> TYPE: DNA
<213> ORGANISM: Triticum sp.

<400> SEQUENCE: 186
atgtgcatgt cggacgc                                                    17

<210> SEQ ID NO 187
<211> LENGTH: 17
<212> TYPE: DNA
<213> ORGANISM: Triticum sp.

<400> SEQUENCE: 187
aggacttccg caccctg                                                    17

<210> SEQ ID NO 188
<211> LENGTH: 19
<212> TYPE: DNA
<213> ORGANISM: Triticum sp.

<400> SEQUENCE: 188
tggcgtggtc taaatggac                                                  19

<210> SEQ ID NO 189
<211> LENGTH: 20
<212> TYPE: DNA
<213> ORGANISM: Triticum sp.

<400> SEQUENCE: 189
caaatggatc gagaaaggga                                                 20

<210> SEQ ID NO 190
<211> LENGTH: 22
<212> TYPE: DNA
<213> ORGANISM: Triticum sp.

<400> SEQUENCE: 190
ctgccatttt tctggatcta cc                                              22

<210> SEQ ID NO 191
<211> LENGTH: 21
<212> TYPE: DNA
<213> ORGANISM: Triticum sp.

<400> SEQUENCE: 191
```

```
caactggttg ctacacaagc a                                              21

<210> SEQ ID NO 192
<211> LENGTH: 21
<212> TYPE: DNA
<213> ORGANISM: Triticum sp.

<400> SEQUENCE: 192
gggatgtctg ttccatctta g                                              21

<210> SEQ ID NO 193
<211> LENGTH: 23
<212> TYPE: DNA
<213> ORGANISM: Triticum sp.

<400> SEQUENCE: 193
caactgtacg taggtttcat tgc                                            23

<210> SEQ ID NO 194
<211> LENGTH: 18
<212> TYPE: DNA
<213> ORGANISM: Triticum sp.

<400> SEQUENCE: 194
tctgccgtaa gtcgcctc                                                  18

<210> SEQ ID NO 195
<211> LENGTH: 18
<212> TYPE: DNA
<213> ORGANISM: Triticum sp.

<400> SEQUENCE: 195
agagtgcatg gtgggacg                                                  18

<210> SEQ ID NO 196
<211> LENGTH: 20
<212> TYPE: DNA
<213> ORGANISM: Triticum sp.

<400> SEQUENCE: 196
ccaagacgat gctgaagtca                                                20

<210> SEQ ID NO 197
<211> LENGTH: 22
<212> TYPE: DNA
<213> ORGANISM: Triticum sp.

<400> SEQUENCE: 197
gatcgcttca tctctctctc tc                                             22

<210> SEQ ID NO 198
<211> LENGTH: 17
<212> TYPE: DNA
<213> ORGANISM: Triticum sp.

<400> SEQUENCE: 198
gtacacgccg taggccc                                                   17

<210> SEQ ID NO 199
<211> LENGTH: 23
<212> TYPE: DNA
<213> ORGANISM: Triticum sp.
```

```
<400> SEQUENCE: 199
agggaaaaga catcttttt ttc                                              23

<210> SEQ ID NO 200
<211> LENGTH: 17
<212> TYPE: DNA
<213> ORGANISM: Triticum sp.

<400> SEQUENCE: 200
cgaccgactt cgggttc                                                    17

<210> SEQ ID NO 201
<211> LENGTH: 17
<212> TYPE: DNA
<213> ORGANISM: Triticum sp.

<400> SEQUENCE: 201 gccccttgc acaaatc                                                     17

<210> SEQ ID NO 202
<211> LENGTH: 17
<212> TYPE: DNA
<213> ORGANISM: Triticum sp.

<400> SEQUENCE: 202
cgcagctaca ggaggcc                                                    17

<210> SEQ ID NO 203
<211> LENGTH: 19
<212> TYPE: DNA
<213> ORGANISM: Triticum sp.

<400> SEQUENCE: 203
ctccctgtac gcctaaggc                                                  19

<210> SEQ ID NO 204
<211> LENGTH: 19
<212> TYPE: DNA
<213> ORGANISM: Triticum sp.

<400> SEQUENCE: 204
ctcgcgctac tagccattg                                                  19

<210> SEQ ID NO 205
<211> LENGTH: 18
<212> TYPE: DNA
<213> ORGANISM: Triticum sp.

<400> SEQUENCE: 205
tctgccgtaa gtcgcctc                                                   18

<210> SEQ ID NO 206
<211> LENGTH: 20
<212> TYPE: DNA
<213> ORGANISM: Triticum sp.

<400> SEQUENCE: 206
ggtttcattg cttgccctaa                                                 20

<210> SEQ ID NO 207
<211> LENGTH: 20
<212> TYPE: DNA
<213> ORGANISM: Triticum sp.
```

<400> SEQUENCE: 207
gagaaacatg ccgaacaaca                                              20

<210> SEQ ID NO 208
<211> LENGTH: 22
<212> TYPE: DNA
<213> ORGANISM: Triticum sp.

<400> SEQUENCE: 208
gcatgcatga gaataggaac tg                                           22

<210> SEQ ID NO 209
<211> LENGTH: 20
<212> TYPE: DNA
<213> ORGANISM: Triticum sp.

<400> SEQUENCE: 209
tgttgcggat ggtcactatt                                              20

<210> SEQ ID NO 210
<211> LENGTH: 21
<212> TYPE: DNA
<213> ORGANISM: Triticum sp.

<400> SEQUENCE: 210
gagtacacat ttggcctctg c                                            21

<210> SEQ ID NO 211
<211> LENGTH: 21
<212> TYPE: DNA
<213> ORGANISM: Triticum sp.

<400> SEQUENCE: 211
aggggatatg ttgtcactcc a                                            21

<210> SEQ ID NO 212
<211> LENGTH: 22
<212> TYPE: DNA
<213> ORGANISM: Triticum sp.

<400> SEQUENCE: 212
ttatgtgatt gcgtacgtac cc                                           22

<210> SEQ ID NO 213
<211> LENGTH: 23
<212> TYPE: DNA
<213> ORGANISM: Triticum sp.

<400> SEQUENCE: 213
tgcatataaa cagtcacaca ccc                                          23

<210> SEQ ID NO 214
<211> LENGTH: 23
<212> TYPE: DNA
<213> ORGANISM: Triticum sp.

<400> SEQUENCE: 214
tttgagctcc aaagtgagtt agc                                          23

<210> SEQ ID NO 215
<211> LENGTH: 18
<212> TYPE: DNA

<210> SEQ ID NO 215
<211> LENGTH: 18
<212> TYPE: DNA
<213> ORGANISM: Triticum sp.

<400> SEQUENCE: 215
caagatcgtg gagccagc                                                 18

<210> SEQ ID NO 216
<211> LENGTH: 20
<212> TYPE: DNA
<213> ORGANISM: Triticum sp.

<400> SEQUENCE: 216
agctgctagc ttttgggaca                                               20

<210> SEQ ID NO 217
<211> LENGTH: 21
<212> TYPE: DNA
<213> ORGANISM: Triticum sp.

<400> SEQUENCE: 217
tgctctttgg cgaatatatg g                                             21

<210> SEQ ID NO 218
<211> LENGTH: 23
<212> TYPE: DNA
<213> ORGANISM: Triticum sp.

<400> SEQUENCE: 218
gttcaaaaca aattaaaagg ccc                                           23

<210> SEQ ID NO 219
<211> LENGTH: 20
<212> TYPE: DNA
<213> ORGANISM: Triticum sp.

<400> SEQUENCE: 219
attggacgga cagatgcttt                                               20

<210> SEQ ID NO 220
<211> LENGTH: 19
<212> TYPE: DNA
<213> ORGANISM: Triticum sp.

<400> SEQUENCE: 220
agcagtgagg aagggatc                                                 19

<210> SEQ ID NO 221
<211> LENGTH: 20
<212> TYPE: DNA
<213> ORGANISM: Triticum sp.

<400> SEQUENCE: 221
aacttgcaaa actgttctga                                               20

<210> SEQ ID NO 222
<211> LENGTH: 20
<212> TYPE: DNA
<213> ORGANISM: Triticum sp.

<400> SEQUENCE: 222
tatttgaagc ggtttgattt                                               20

<210> SEQ ID NO 223
<211> LENGTH: 22

```
<212> TYPE: DNA
<213> ORGANISM: Triticum sp.

<400> SEQUENCE: 223
aattttcttc ctcacttatt ct                                              22

<210> SEQ ID NO 224
<211> LENGTH: 17
<212> TYPE: DNA
<213> ORGANISM: Triticum sp.

<400> SEQUENCE: 224
aacaaaaaat tagggcc                                                    17

<210> SEQ ID NO 225
<211> LENGTH: 20
<212> TYPE: DNA
<213> ORGANISM: Triticum sp.

<400> SEQUENCE: 225
atttgcctga agaaaatatt                                                 20

<210> SEQ ID NO 226
<211> LENGTH: 20
<212> TYPE: DNA
<213> ORGANISM: Triticum sp.

<400> SEQUENCE: 226
aatttcactg catacacaag                                                 20

<210> SEQ ID NO 227
<211> LENGTH: 20
<212> TYPE: DNA
<213> ORGANISM: Triticum sp.

<400> SEQUENCE: 227
gttgcttcat gaacgctcaa                                                 20

<210> SEQ ID NO 228
<211> LENGTH: 20
<212> TYPE: DNA
<213> ORGANISM: Triticum sp.

<400> SEQUENCE: 228
ctgcccaatt ttctccactc                                                 20

<210> SEQ ID NO 229
<211> LENGTH: 23
<212> TYPE: DNA
<213> ORGANISM: Triticum sp.

<400> SEQUENCE: 229
cggccatatt tctgtaagta tgc                                             23

<210> SEQ ID NO 230
<211> LENGTH: 17
<212> TYPE: DNA
<213> ORGANISM: Triticum sp.

<400> SEQUENCE: 230
gcaggtaatg gccggac                                                    17

<210> SEQ ID NO 231
```

```
<211> LENGTH: 17
<212> TYPE: DNA
<213> ORGANISM: Triticum sp.

<400> SEQUENCE: 231
ttggccgtgt aaggcag                                                    17

<210> SEQ ID NO 232
<211> LENGTH: 23
<212> TYPE: DNA
<213> ORGANISM: Triticum sp.

<400> SEQUENCE: 232
tctcattcac acacaacact agc                                             23

<210> SEQ ID NO 233
<211> LENGTH: 21
<212> TYPE: DNA
<213> ORGANISM: Triticum sp.

<400> SEQUENCE: 233
aatgaaaaaa cacttgcgtg g                                               21

<210> SEQ ID NO 234
<211> LENGTH: 20
<212> TYPE: DNA
<213> ORGANISM: Triticum sp.

<400> SEQUENCE: 234
gcacattttt cactttcggg                                                 20

<210> SEQ ID NO 235
<211> LENGTH: 20
<212> TYPE: DNA
<213> ORGANISM: Triticum sp.

<400> SEQUENCE: 235
atgacccttc tgccaaacac                                                 20

<210> SEQ ID NO 236
<211> LENGTH: 18
<212> TYPE: DNA
<213> ORGANISM: Triticum sp.

<400> SEQUENCE: 236
atcgaccggg atctagcc                                                   18

<210> SEQ ID NO 237
<211> LENGTH: 19
<212> TYPE: DNA
<213> ORGANISM: Triticum sp.

<400> SEQUENCE: 237
catccctacg ccactctgc                                                  19

<210> SEQ ID NO 238
<211> LENGTH: 21
<212> TYPE: DNA
<213> ORGANISM: Triticum sp.

<400> SEQUENCE: 238
aatggtatct attccgaccc g                                               21
```

-continued

<210> SEQ ID NO 239
<211> LENGTH: 17
<212> TYPE: DNA
<213> ORGANISM: Triticum sp.

<400> SEQUENCE: 239
tcaccgtggt caccgac                                                17

<210> SEQ ID NO 240
<211> LENGTH: 20
<212> TYPE: DNA
<213> ORGANISM: Triticum sp.

<400> SEQUENCE: 240
ccaccgagcc gataatgtac                                             20

<210> SEQ ID NO 241
<211> LENGTH: 20
<212> TYPE: DNA
<213> ORGANISM: Triticum sp.

<400> SEQUENCE: 241
tactggttca cattggtgcg                                             20

<210> SEQ ID NO 242
<211> LENGTH: 19
<212> TYPE: DNA
<213> ORGANISM: Triticum sp.

<400> SEQUENCE: 242
tcgccatcac tcgttcaag                                              19

<210> SEQ ID NO 243
<211> LENGTH: 23
<212> TYPE: DNA
<213> ORGANISM: Triticum sp.

<400> SEQUENCE: 243
ggattggagt taagagagaa ccg                                         23

<210> SEQ ID NO 244
<211> LENGTH: 20
<212> TYPE: DNA
<213> ORGANISM: Triticum sp.

<400> SEQUENCE: 244
gcagagtgat caatgccaga                                             20

<210> SEQ ID NO 245
<211> LENGTH: 20
<212> TYPE: DNA
<213> ORGANISM: Triticum sp.

<400> SEQUENCE: 245
gtgaagcaga cccacaacac                                             20

<210> SEQ ID NO 246
<211> LENGTH: 18
<212> TYPE: DNA
<213> ORGANISM: Triticum sp.

<400> SEQUENCE: 246
gacggctgcg acgtagag                                               18

```
<210> SEQ ID NO 247
<211> LENGTH: 21
<212> TYPE: DNA
<213> ORGANISM: Triticum sp.

<400> SEQUENCE: 247
aattcaacct accaatctct g                                              21

<210> SEQ ID NO 248
<211> LENGTH: 21
<212> TYPE: DNA
<213> ORGANISM: Triticum sp.

<400> SEQUENCE: 248
gcctaataaa ctgaaaacga g                                              21

<210> SEQ ID NO 249
<211> LENGTH: 21
<212> TYPE: DNA
<213> ORGANISM: Triticum sp.

<400> SEQUENCE: 249
atcgtcacgt attttgcaat g                                              21

<210> SEQ ID NO 250
<211> LENGTH: 22
<212> TYPE: DNA
<213> ORGANISM: Triticum sp.

<400> SEQUENCE: 250
tgcgtaagtc tagcattttc tg                                             22

<210> SEQ ID NO 251
<211> LENGTH: 19
<212> TYPE: DNA
<213> ORGANISM: Triticum sp.

<400> SEQUENCE: 251
actacttagg cctcccgcc                                                 19

<210> SEQ ID NO 252
<211> LENGTH: 20
<212> TYPE: DNA
<213> ORGANISM: Triticum sp.

<400> SEQUENCE: 252
tgacccactt gcaattcatc                                                20

<210> SEQ ID NO 253
<211> LENGTH: 20
<212> TYPE: DNA
<213> ORGANISM: Triticum sp.

<400> SEQUENCE: 253
gaggagtaag acacatgccc                                                20

<210> SEQ ID NO 254
<211> LENGTH: 20
<212> TYPE: DNA
<213> ORGANISM: Triticum sp.

<400> SEQUENCE: 254
gtggctggag attcaggttc                                                20
```

<210> SEQ ID NO 255
<211> LENGTH: 21
<212> TYPE: DNA
<213> ORGANISM: Triticum sp.

<400> SEQUENCE: 255
gcaagaagca acagcagtaa c                                              21

<210> SEQ ID NO 256
<211> LENGTH: 20
<212> TYPE: DNA
<213> ORGANISM: Triticum sp.

<400> SEQUENCE: 256
cagatgctct tctctgctgg                                                20

<210> SEQ ID NO 257
<211> LENGTH: 20
<212> TYPE: DNA
<213> ORGANISM: Triticum sp.

<400> SEQUENCE: 257
aggaaacaga aatatcgcgg                                                20

<210> SEQ ID NO 258
<211> LENGTH: 20
<212> TYPE: DNA
<213> ORGANISM: Triticum sp.

<400> SEQUENCE: 258
aggactgtgg ggaatgaatg                                                20

<210> SEQ ID NO 259
<211> LENGTH: 18
<212> TYPE: DNA
<213> ORGANISM: Triticum sp.

<400> SEQUENCE: 259
tcacgtggaa gacgctcc                                                  18

<210> SEQ ID NO 260
<211> LENGTH: 20
<212> TYPE: DNA
<213> ORGANISM: Triticum sp.

<400> SEQUENCE: 260
ctacgtgcac caccattttg                                                20

<210> SEQ ID NO 261
<211> LENGTH: 20
<212> TYPE: DNA
<213> ORGANISM: Triticum sp.

<400> SEQUENCE: 261
atcgcatgat gcacgtagag                                                20

<210> SEQ ID NO 262
<211> LENGTH: 21
<212> TYPE: DNA
<213> ORGANISM: Triticum sp.

<400> SEQUENCE: 262

| | |
|---|---|
| acatgcatgc ctacctaatg g | 21 |

<210> SEQ ID NO 263
<211> LENGTH: 20
<212> TYPE: DNA
<213> ORGANISM: Triticum sp.

<400> SEQUENCE: 263

| | |
|---|---|
| ccgccctcat taagtttcac | 20 |

<210> SEQ ID NO 264
<211> LENGTH: 22
<212> TYPE: DNA
<213> ORGANISM: Triticum sp.

<400> SEQUENCE: 264

| | |
|---|---|
| tttgacaagt acacgagtct gc | 22 |

<210> SEQ ID NO 265
<211> LENGTH: 19
<212> TYPE: DNA
<213> ORGANISM: Triticum sp.

<400> SEQUENCE: 265

| | |
|---|---|
| aggagctcct ctgtgccac | 19 |

<210> SEQ ID NO 266
<211> LENGTH: 19
<212> TYPE: DNA
<213> ORGANISM: Triticum sp.

<400> SEQUENCE: 266

| | |
|---|---|
| ttcgggactc tcttccctg | 19 |

<210> SEQ ID NO 267
<211> LENGTH: 22
<212> TYPE: DNA
<213> ORGANISM: Triticum sp.

<400> SEQUENCE: 267

| | |
|---|---|
| catggacatt ttaccacaag ac | 22 |

<210> SEQ ID NO 268
<211> LENGTH: 17
<212> TYPE: DNA
<213> ORGANISM: Triticum sp.

<400> SEQUENCE: 268

| | |
|---|---|
| tgcgtgtggt ccacctc | 17 |

<210> SEQ ID NO 269
<211> LENGTH: 22
<212> TYPE: DNA
<213> ORGANISM: Triticum sp.

<400> SEQUENCE: 269

| | |
|---|---|
| ggttgctgta caagtgttca cg | 22 |

<210> SEQ ID NO 270
<211> LENGTH: 20
<212> TYPE: DNA
<213> ORGANISM: Triticum sp.

<400> SEQUENCE: 270
cgggtgctgt gtgtaatgac                                            20

<210> SEQ ID NO 271
<211> LENGTH: 22
<212> TYPE: DNA
<213> ORGANISM: Triticum sp.

<400> SEQUENCE: 271
cgagatacta tggaaggtga gg                                         22

<210> SEQ ID NO 272
<211> LENGTH: 19
<212> TYPE: DNA
<213> ORGANISM: Triticum sp.

<400> SEQUENCE: 272
atctttgcaa ggattgccc                                             19

<210> SEQ ID NO 273
<211> LENGTH: 19
<212> TYPE: DNA
<213> ORGANISM: Triticum sp.

<400> SEQUENCE: 273
caatgtggag acggtgtgc                                             19

<210> SEQ ID NO 274
<211> LENGTH: 18
<212> TYPE: DNA
<213> ORGANISM: Triticum sp.

<400> SEQUENCE: 274
tgttgcatgc gatcatgc                                              18

<210> SEQ ID NO 275
<211> LENGTH: 22
<212> TYPE: DNA
<213> ORGANISM: Triticum sp.

<400> SEQUENCE: 275
tcacaaaatg atttctcatc cg                                         22

<210> SEQ ID NO 276
<211> LENGTH: 19
<212> TYPE: DNA
<213> ORGANISM: Triticum sp.

<400> SEQUENCE: 276
tgcagaaaac caacaaggg                                             19

<210> SEQ ID NO 277
<211> LENGTH: 22
<212> TYPE: DNA
<213> ORGANISM: Triticum sp.

<400> SEQUENCE: 277
tttcttctgt cgttctcttc cc                                         22

<210> SEQ ID NO 278
<211> LENGTH: 19
<212> TYPE: DNA
<213> ORGANISM: Triticum sp.

```
<400> SEQUENCE: 278
tttttacgcg tcaacgacg                                                   19

<210> SEQ ID NO 279
<211> LENGTH: 20
<212> TYPE: DNA
<213> ORGANISM: Triticum sp.

<400> SEQUENCE: 279
gcaatccacg agaagagagg                                                  20

<210> SEQ ID NO 280
<211> LENGTH: 21
<212> TYPE: DNA
<213> ORGANISM: Triticum sp.

<400> SEQUENCE: 280
cacaaactct tgacatgtgc g                                                21

<210> SEQ ID NO 281
<211> LENGTH: 20
<212> TYPE: DNA
<213> ORGANISM: Triticum sp.

<400> SEQUENCE: 281
ttgctatcca tgtgccagag                                                  20

<210> SEQ ID NO 282
<211> LENGTH: 21
<212> TYPE: DNA
<213> ORGANISM: Triticum sp.

<400> SEQUENCE: 282
acatgtttca tgcaggtagc c                                                21

<210> SEQ ID NO 283
<211> LENGTH: 20
<212> TYPE: DNA
<213> ORGANISM: Triticum sp.

<400> SEQUENCE: 283
agccagcaag tcaccaaaac                                                  20

<210> SEQ ID NO 284
<211> LENGTH: 23
<212> TYPE: DNA
<213> ORGANISM: Triticum sp.

<400> SEQUENCE: 284
agtgctggaa agagtagtga agc                                              23

<210> SEQ ID NO 285
<211> LENGTH: 18
<212> TYPE: DNA
<213> ORGANISM: Triticum sp.

<400> SEQUENCE: 285
gcccggtcat gtaaaacg                                                    18

<210> SEQ ID NO 286
<211> LENGTH: 22
<212> TYPE: DNA
<213> ORGANISM: Triticum sp.
```

```
<400> SEQUENCE: 286
tttcagtttg cgttaagctt tg                                              22

<210> SEQ ID NO 287
<211> LENGTH: 20
<212> TYPE: DNA
<213> ORGANISM: Triticum sp.

<400> SEQUENCE: 287
aatttcaaaa aggagagaga                                                 20

<210> SEQ ID NO 288
<211> LENGTH: 20
<212> TYPE: DNA
<213> ORGANISM: Triticum sp.

<400> SEQUENCE: 288
aacatgtgtt tttagctatc                                                 20

<210> SEQ ID NO 289
<211> LENGTH: 19
<212> TYPE: DNA
<213> ORGANISM: Triticum sp.

<400> SEQUENCE: 289
cgtactccac tccacacgg                                                  19

<210> SEQ ID NO 290
<211> LENGTH: 20
<212> TYPE: DNA
<213> ORGANISM: Triticum sp.

<400> SEQUENCE: 290
cggtccaagt gctacctttc                                                 20

<210> SEQ ID NO 291
<211> LENGTH: 20
<212> TYPE: DNA
<213> ORGANISM: Triticum sp.

<400> SEQUENCE: 291
ccctttaatc tcgctccctc                                                 20

<210> SEQ ID NO 292
<211> LENGTH: 22
<212> TYPE: DNA
<213> ORGANISM: Triticum sp.

<400> SEQUENCE: 292
gtctctttct cgtacttcca gg                                              22

<210> SEQ ID NO 293
<211> LENGTH: 21
<212> TYPE: DNA
<213> ORGANISM: Triticum sp.

<400> SEQUENCE: 293
cctcttcctc cctcacttag c                                               21

<210> SEQ ID NO 294
<211> LENGTH: 18
<212> TYPE: DNA
```

```
<213> ORGANISM: Triticum sp.

<400> SEQUENCE: 294
tgctaactgg cctttgcc                                              18

<210> SEQ ID NO 295
<211> LENGTH: 20
<212> TYPE: DNA
<213> ORGANISM: Triticum sp.

<400> SEQUENCE: 295
aattttcttc ctcacttatt                                            20

<210> SEQ ID NO 296
<211> LENGTH: 20
<212> TYPE: DNA
<213> ORGANISM: Triticum sp.

<400> SEQUENCE: 296
aaacgaacaa ccactcaatc                                            20

<210> SEQ ID NO 297
<211> LENGTH: 21
<212> TYPE: DNA
<213> ORGANISM: Triticum sp.

<400> SEQUENCE: 297
gcaatctttt ttctgaccac g                                          21

<210> SEQ ID NO 298
<211> LENGTH: 20
<212> TYPE: DNA
<213> ORGANISM: Triticum sp.

<400> SEQUENCE: 298
acgaggcaag aacacacatg                                            20

<210> SEQ ID NO 299
<211> LENGTH: 19
<212> TYPE: DNA
<213> ORGANISM: Triticum sp.

<400> SEQUENCE: 299
ttcagtggta gcggtcgag                                             19

<210> SEQ ID NO 300
<211> LENGTH: 20
<212> TYPE: DNA
<213> ORGANISM: Triticum sp.

<400> SEQUENCE: 300
ccgacatctc atggatccac                                            20

<210> SEQ ID NO 301
<211> LENGTH: 19
<212> TYPE: DNA
<213> ORGANISM: Triticum sp.

<400> SEQUENCE: 301
tatccagagc agacggacg                                             19

<210> SEQ ID NO 302
<211> LENGTH: 20
```

```
<212> TYPE: DNA
<213> ORGANISM: Triticum sp.

<400> SEQUENCE: 302
ggtctagctt cgacgacacc                                           20

<210> SEQ ID NO 303
<211> LENGTH: 20
<212> TYPE: DNA
<213> ORGANISM: Triticum sp.

<400> SEQUENCE: 303
caaggaaata ggcggtaact                                           20

<210> SEQ ID NO 304
<211> LENGTH: 20
<212> TYPE: DNA
<213> ORGANISM: Triticum sp.

<400> SEQUENCE: 304
atttgagtct gaagtttgca                                           20

<210> SEQ ID NO 305
<211> LENGTH: 22
<212> TYPE: DNA
<213> ORGANISM: Triticum sp.

<400> SEQUENCE: 305
caagcaaggt ttcgttttat cc                                        22

<210> SEQ ID NO 306
<211> LENGTH: 20
<212> TYPE: DNA
<213> ORGANISM: Triticum sp.

<400> SEQUENCE: 306
gcatgtggtc catgtactgc                                           20

<210> SEQ ID NO 307
<211> LENGTH: 20
<212> TYPE: DNA
<213> ORGANISM: Triticum sp.

<400> SEQUENCE: 307
ggcttccaga aaacaacagg                                           20

<210> SEQ ID NO 308
<211> LENGTH: 20
<212> TYPE: DNA
<213> ORGANISM: Triticum sp.

<400> SEQUENCE: 308
atcggtgcgt accatcctac                                           20

<210> SEQ ID NO 309
<211> LENGTH: 21
<212> TYPE: DNA
<213> ORGANISM: Triticum sp.

<400> SEQUENCE: 309
acctcatcca catgttctac g                                         21

<210> SEQ ID NO 310
```

```
<211> LENGTH: 17
<212> TYPE: DNA
<213> ORGANISM: Triticum sp.

<400> SEQUENCE: 310
gcatggatag gacgccc                                                      17

<210> SEQ ID NO 311
<211> LENGTH: 21
<212> TYPE: DNA
<213> ORGANISM: Triticum sp.

<400> SEQUENCE: 311
ccatgttgag taggttcagc c                                                 21

<210> SEQ ID NO 312
<211> LENGTH: 20
<212> TYPE: DNA
<213> ORGANISM: Triticum sp.

<400> SEQUENCE: 312
cttggccaga agctacgaac                                                   20

<210> SEQ ID NO 313
<211> LENGTH: 21
<212> TYPE: DNA
<213> ORGANISM: Triticum sp.

<400> SEQUENCE: 313
agcgttcttg ggaattagag a                                                 21

<210> SEQ ID NO 314
<211> LENGTH: 19
<212> TYPE: DNA
<213> ORGANISM: Triticum sp.

<400> SEQUENCE: 314
ccaatcagcc tgcaacaac                                                    19

<210> SEQ ID NO 315
<211> LENGTH: 21
<212> TYPE: DNA
<213> ORGANISM: Triticum sp.

<400> SEQUENCE: 315
tatggtcaaa gttggacctc g                                                 21

<210> SEQ ID NO 316
<211> LENGTH: 20
<212> TYPE: DNA
<213> ORGANISM: Triticum sp.

<400> SEQUENCE: 316
aggctgcagc tcttcttcag                                                   20

<210> SEQ ID NO 317
<211> LENGTH: 20
<212> TYPE: DNA
<213> ORGANISM: Triticum sp.

<400> SEQUENCE: 317
aaacagcgga tttcatcgag                                                   20
```

<210> SEQ ID NO 318
<211> LENGTH: 20
<212> TYPE: DNA
<213> ORGANISM: Triticum sp.

<400> SEQUENCE: 318
tccgctgttg ttctgatctc                                           20

<210> SEQ ID NO 319
<211> LENGTH: 21
<212> TYPE: DNA
<213> ORGANISM: Triticum sp.

<400> SEQUENCE: 319
ctaattgcaa caggtcatgg g                                         21

<210> SEQ ID NO 320
<211> LENGTH: 22
<212> TYPE: DNA
<213> ORGANISM: Triticum sp.

<400> SEQUENCE: 320
tacttgtgtt ctgggacaat gg                                        22

<210> SEQ ID NO 321
<211> LENGTH: 20
<212> TYPE: DNA
<213> ORGANISM: Triticum sp.

<400> SEQUENCE: 321
gtaacttgtt gccaaagggg                                           20

<210> SEQ ID NO 322
<211> LENGTH: 21
<212> TYPE: DNA
<213> ORGANISM: Triticum sp.

<400> SEQUENCE: 322
acaaagtggc aaaaggagac a                                         21

<210> SEQ ID NO 323
<211> LENGTH: 20
<212> TYPE: DNA
<213> ORGANISM: Triticum sp.

<400> SEQUENCE: 323
ccatttcacc taatgcctgc                                           20

<210> SEQ ID NO 324
<211> LENGTH: 23
<212> TYPE: DNA
<213> ORGANISM: Triticum sp.

<400> SEQUENCE: 324
aataaaacca tgagctcact tgc                                       23

<210> SEQ ID NO 325
<211> LENGTH: 18
<212> TYPE: DNA
<213> ORGANISM: Triticum sp.

<400> SEQUENCE: 325
ctgcaggcca tgatgatg                                             18

```
<210> SEQ ID NO 326
<211> LENGTH: 18
<212> TYPE: DNA
<213> ORGANISM: Triticum sp.

<400> SEQUENCE: 326
accgtgggtg ttgtgagc                                                 18

<210> SEQ ID NO 327
<211> LENGTH: 22
<212> TYPE: DNA
<213> ORGANISM: Triticum sp.

<400> SEQUENCE: 327
gaccaagata ttcaaactgg cc                                            22

<210> SEQ ID NO 328
<211> LENGTH: 20
<212> TYPE: DNA
<213> ORGANISM: Triticum sp.

<400> SEQUENCE: 328
agctcagctt gcttggtacc                                               20

<210> SEQ ID NO 329
<211> LENGTH: 20
<212> TYPE: DNA
<213> ORGANISM: Triticum sp.

<400> SEQUENCE: 329
aatagagccc tgggactggg                                               20

<210> SEQ ID NO 330
<211> LENGTH: 20
<212> TYPE: DNA
<213> ORGANISM: Triticum sp.

<400> SEQUENCE: 330
gaaggacgac attccacctg                                               20

<210> SEQ ID NO 331
<211> LENGTH: 22
<212> TYPE: DNA
<213> ORGANISM: Triticum sp.

<400> SEQUENCE: 331
atagtgtgtt gcatgctgtg tg                                            22

<210> SEQ ID NO 332
<211> LENGTH: 20
<212> TYPE: DNA
<213> ORGANISM: Triticum sp.

<400> SEQUENCE: 332
tctaattagc gttggctgcc                                               20

<210> SEQ ID NO 333
<211> LENGTH: 22
<212> TYPE: DNA
<213> ORGANISM: Triticum sp.

<400> SEQUENCE: 333
attggcgact ctagcatata cg                                            22
```

<210> SEQ ID NO 334
<211> LENGTH: 22
<212> TYPE: DNA
<213> ORGANISM: Triticum sp.

<400> SEQUENCE: 334
gggatgtctg ttccatctta gc                                              22

<210> SEQ ID NO 335
<211> LENGTH: 20
<212> TYPE: DNA
<213> ORGANISM: Triticum sp.

<400> SEQUENCE: 335
gggctagaaa acaggaaggc                                                 20

<210> SEQ ID NO 336
<211> LENGTH: 18
<212> TYPE: DNA
<213> ORGANISM: Triticum sp.

<400> SEQUENCE: 336
tctcccggag ggtaggag                                                   18

<210> SEQ ID NO 337
<211> LENGTH: 20
<212> TYPE: DNA
<213> ORGANISM: Triticum sp.

<400> SEQUENCE: 337
gtcagataac gccgtccaat                                                 20

<210> SEQ ID NO 338
<211> LENGTH: 20
<212> TYPE: DNA
<213> ORGANISM: Triticum sp.

<400> SEQUENCE: 338
ctacgtgcac caccattttg                                                 20

<210> SEQ ID NO 339
<211> LENGTH: 20
<212> TYPE: DNA
<213> ORGANISM: Triticum sp.

<400> SEQUENCE: 339
acgccagttg atccgtaaac                                                 20

<210> SEQ ID NO 340
<211> LENGTH: 21
<212> TYPE: DNA
<213> ORGANISM: Triticum sp.

<400> SEQUENCE: 340
gacatcaata accgtggatg g                                               21

<210> SEQ ID NO 341
<211> LENGTH: 20
<212> TYPE: DNA
<213> ORGANISM: Triticum sp.

<400> SEQUENCE: 341
ttttcattgt gccctctact                      20

<210> SEQ ID NO 342
<211> LENGTH: 22
<212> TYPE: DNA
<213> ORGANISM: Triticum sp.

<400> SEQUENCE: 342
gccaagtttc ttagctagtt aa                   22

<210> SEQ ID NO 343
<211> LENGTH: 21
<212> TYPE: DNA
<213> ORGANISM: Triticum sp.

<400> SEQUENCE: 343
ctacaattcg aaggagaggg g                    21

<210> SEQ ID NO 344
<211> LENGTH: 21
<212> TYPE: DNA
<213> ORGANISM: Triticum sp.

<400> SEQUENCE: 344
caccgcgtca actacttaag c                    21

<210> SEQ ID NO 345
<211> LENGTH: 21
<212> TYPE: DNA
<213> ORGANISM: Triticum sp.

<400> SEQUENCE: 345
atcatgtcga tctccttgac g                    21

<210> SEQ ID NO 346
<211> LENGTH: 20
<212> TYPE: DNA
<213> ORGANISM: Triticum sp.

<400> SEQUENCE: 346
tgccatgcac attagcagat                      20

<210> SEQ ID NO 347
<211> LENGTH: 22
<212> TYPE: DNA
<213> ORGANISM: Triticum sp.

<400> SEQUENCE: 347
aagtttcaca caagatctct cc                   22

<210> SEQ ID NO 348
<211> LENGTH: 20
<212> TYPE: DNA
<213> ORGANISM: Triticum sp.

<400> SEQUENCE: 348
tgacaagtac acgagtctgc                      20

<210> SEQ ID NO 349
<211> LENGTH: 22
<212> TYPE: DNA
<213> ORGANISM: Triticum sp.

<400> SEQUENCE: 349

```
atagcgaagt ctccctactc ca                                          22

<210> SEQ ID NO 350
<211> LENGTH: 17
<212> TYPE: DNA
<213> ORGANISM: Triticum sp.

<400> SEQUENCE: 350
atgtgcatgt cggacgc                                                17

<210> SEQ ID NO 351
<211> LENGTH: 21
<212> TYPE: DNA
<213> ORGANISM: Triticum sp.

<400> SEQUENCE: 351
tcatctgcta tttgtgctac a                                           21

<210> SEQ ID NO 352
<211> LENGTH: 19
<212> TYPE: DNA
<213> ORGANISM: Triticum sp.

<400> SEQUENCE: 352
tcaaatacac caatgtgcc                                              19

<210> SEQ ID NO 353
<211> LENGTH: 20
<212> TYPE: DNA
<213> ORGANISM: Triticum sp.

<400> SEQUENCE: 353
tacaaccgca agtaatgcca                                             20

<210> SEQ ID NO 354
<211> LENGTH: 20
<212> TYPE: DNA
<213> ORGANISM: Triticum sp.

<400> SEQUENCE: 354
taccaacacc ctagcccttg                                             20

<210> SEQ ID NO 355
<211> LENGTH: 21
<212> TYPE: DNA
<213> ORGANISM: Triticum sp.

<400> SEQUENCE: 355
tgtcatggat tatttggtcg g                                           21

<210> SEQ ID NO 356
<211> LENGTH: 21
<212> TYPE: DNA
<213> ORGANISM: Triticum sp.

<400> SEQUENCE: 356
ctgcactctc ggtataccag c                                           21

<210> SEQ ID NO 357
<211> LENGTH: 17
<212> TYPE: DNA
<213> ORGANISM: Triticum sp.
```

-continued

```
<400> SEQUENCE: 357
gtgctgccac cacttgc                                                  17

<210> SEQ ID NO 358
<211> LENGTH: 19
<212> TYPE: DNA
<213> ORGANISM: Triticum sp.

<400> SEQUENCE: 358
tgtaggcact gcttgggag                                                19

<210> SEQ ID NO 359
<211> LENGTH: 17
<212> TYPE: DNA
<213> ORGANISM: Triticum sp.

<400> SEQUENCE: 359
cgacattggc ttcggtg                                                  17

<210> SEQ ID NO 360
<211> LENGTH: 20
<212> TYPE: DNA
<213> ORGANISM: Triticum sp.

<400> SEQUENCE: 360
ataaaacagt gcggtccagg                                               20

<210> SEQ ID NO 361
<211> LENGTH: 20
<212> TYPE: DNA
<213> ORGANISM: Triticum sp.

<400> SEQUENCE: 361
tcgatttatt tgggccactg                                               20

<210> SEQ ID NO 362
<211> LENGTH: 22
<212> TYPE: DNA
<213> ORGANISM: Triticum sp.

<400> SEQUENCE: 362
gtataattcg ttcacagcac gc                                            22

<210> SEQ ID NO 363
<211> LENGTH: 18
<212> TYPE: DNA
<213> ORGANISM: Triticum sp.

<400> SEQUENCE: 363
gcttgagacc ggcacagt                                                 18

<210> SEQ ID NO 364
<211> LENGTH: 20
<212> TYPE: DNA
<213> ORGANISM: Triticum sp.

<400> SEQUENCE: 364
cgagaccttg agggtctaga                                               20

<210> SEQ ID NO 365
<211> LENGTH: 21
<212> TYPE: DNA
<213> ORGANISM: Triticum sp.
```

<400> SEQUENCE: 365
cccatacgat gatgtgtttc c                                              21

<210> SEQ ID NO 366
<211> LENGTH: 18
<212> TYPE: DNA
<213> ORGANISM: Triticum sp.

<400> SEQUENCE: 366
caaacggaac atggtccc                                                  18

<210> SEQ ID NO 367
<211> LENGTH: 22
<212> TYPE: DNA
<213> ORGANISM: Triticum sp.

<400> SEQUENCE: 367
atcaacaagg tttgtgtgtt gg                                             22

<210> SEQ ID NO 368
<211> LENGTH: 17
<212> TYPE: DNA
<213> ORGANISM: Triticum sp.

<400> SEQUENCE: 368
atgaaacgcg acctccc                                                   17

<210> SEQ ID NO 369
<211> LENGTH: 21
<212> TYPE: DNA
<213> ORGANISM: Triticum sp.

<400> SEQUENCE: 369
tgcttgtcta gattgcttgg g                                              21

<210> SEQ ID NO 370
<211> LENGTH: 19
<212> TYPE: DNA
<213> ORGANISM: Triticum sp.

<400> SEQUENCE: 370
gatcgtctcg tccttggca                                                 19

<210> SEQ ID NO 371
<211> LENGTH: 17
<212> TYPE: DNA
<213> ORGANISM: Triticum sp.

<400> SEQUENCE: 371
gatctcccat gtccgcc                                                   17

<210> SEQ ID NO 372
<211> LENGTH: 20
<212> TYPE: DNA
<213> ORGANISM: Triticum sp.

<400> SEQUENCE: 372
cgacagtcgt cacttgccta                                                20

<210> SEQ ID NO 373
<211> LENGTH: 17
<212> TYPE: DNA

<213> ORGANISM: Triticum sp.

<400> SEQUENCE: 373
gagcccacaa gctggca        17

<210> SEQ ID NO 374
<211> LENGTH: 18
<212> TYPE: DNA
<213> ORGANISM: Triticum sp.

<400> SEQUENCE: 374
tcgttctccc aaggcttg        18

<210> SEQ ID NO 375
<211> LENGTH: 23
<212> TYPE: DNA
<213> ORGANISM: Triticum sp.

<400> SEQUENCE: 375
aaacttagaa ctgtaatttc aga        23

<210> SEQ ID NO 376
<211> LENGTH: 20
<212> TYPE: DNA
<213> ORGANISM: Triticum sp.

<400> SEQUENCE: 376
agtgtgttca tttgacagtt        20

<210> SEQ ID NO 377
<211> LENGTH: 17
<212> TYPE: DNA
<213> ORGANISM: Triticum sp.

<400> SEQUENCE: 377
cgaggcagcg aggattt        17

<210> SEQ ID NO 378
<211> LENGTH: 17
<212> TYPE: DNA
<213> ORGANISM: Triticum sp.

<400> SEQUENCE: 378
ttctccacta gccccgc        17

<210> SEQ ID NO 379
<211> LENGTH: 21
<212> TYPE: DNA
<213> ORGANISM: Triticum sp.

<400> SEQUENCE: 379
ttgtacatta agttcccatt a        21

<210> SEQ ID NO 380
<211> LENGTH: 20
<212> TYPE: DNA
<213> ORGANISM: Triticum sp.

<400> SEQUENCE: 380
tttaaggacc tacatgacac        20

<210> SEQ ID NO 381
<211> LENGTH: 20

-continued

```
<212> TYPE: DNA
<213> ORGANISM: Triticum sp.

<400> SEQUENCE: 381
atgagttccg ccaaagaatg                                              20

<210> SEQ ID NO 382
<211> LENGTH: 21
<212> TYPE: DNA
<213> ORGANISM: Triticum sp.

<400> SEQUENCE: 382
acgaaataca caagtgggac a                                            21

<210> SEQ ID NO 383
<211> LENGTH: 22
<212> TYPE: DNA
<213> ORGANISM: Triticum sp.

<400> SEQUENCE: 383
gatcaagact tttgtatctc tc                                           22

<210> SEQ ID NO 384
<211> LENGTH: 20
<212> TYPE: DNA
<213> ORGANISM: Triticum sp.

<400> SEQUENCE: 384
gatgtccaac agttagctta                                              20

<210> SEQ ID NO 385
<211> LENGTH: 21
<212> TYPE: DNA
<213> ORGANISM: Triticum sp.

<400> SEQUENCE: 385
cctatggtct ccatcatgag g                                            21

<210> SEQ ID NO 386
<211> LENGTH: 21
<212> TYPE: DNA
<213> ORGANISM: Triticum sp.

<400> SEQUENCE: 386
tcatgtcaac tcaagaacac g                                            21

<210> SEQ ID NO 387
<211> LENGTH: 20
<212> TYPE: DNA
<213> ORGANISM: Triticum sp.

<400> SEQUENCE: 387
gggtcttcat ccggaactct                                              20

<210> SEQ ID NO 388
<211> LENGTH: 21
<212> TYPE: DNA
<213> ORGANISM: Triticum sp.

<400> SEQUENCE: 388
ccatgattta taaattccac c                                            21

<210> SEQ ID NO 389
```

-continued

```
<211> LENGTH: 21
<212> TYPE: DNA
<213> ORGANISM: Triticum sp.

<400> SEQUENCE: 389
tttgttgggg gttaggatta g                                              21

<210> SEQ ID NO 390
<211> LENGTH: 22
<212> TYPE: DNA
<213> ORGANISM: Triticum sp.

<400> SEQUENCE: 390
ccttaacact tgctggtagt ga                                             22

<210> SEQ ID NO 391
<211> LENGTH: 21
<212> TYPE: DNA
<213> ORGANISM: Triticum sp.

<400> SEQUENCE: 391
aaaccatatt gggaggaaag g                                              21

<210> SEQ ID NO 392
<211> LENGTH: 20
<212> TYPE: DNA
<213> ORGANISM: Triticum sp.

<400> SEQUENCE: 392
cacatggcat cacatttgtg                                                20

<210> SEQ ID NO 393
<211> LENGTH: 20
<212> TYPE: DNA
<213> ORGANISM: Triticum sp.

<400> SEQUENCE: 393
attcggttcg ctagctacca                                                20

<210> SEQ ID NO 394
<211> LENGTH: 17
<212> TYPE: DNA
<213> ORGANISM: Triticum sp.

<400> SEQUENCE: 394
acggagagca acctgcc                                                   17

<210> SEQ ID NO 395
<211> LENGTH: 22
<212> TYPE: DNA
<213> ORGANISM: Triticum sp.

<400> SEQUENCE: 395
tctgaacatt acacaaccct ga                                             22

<210> SEQ ID NO 396
<211> LENGTH: 21
<212> TYPE: DNA
<213> ORGANISM: Triticum sp.

<400> SEQUENCE: 396
tgctctctct gaacctgaag c                                              21
```

```
<210> SEQ ID NO 397
<211> LENGTH: 22
<212> TYPE: DNA
<213> ORGANISM: Triticum sp.

<400> SEQUENCE: 397
aatggcaatt ggaagacata gc                                          22

<210> SEQ ID NO 398
<211> LENGTH: 19
<212> TYPE: DNA
<213> ORGANISM: Triticum sp.

<400> SEQUENCE: 398
ttcgcaatgt tgatttggc                                              19

<210> SEQ ID NO 399
<211> LENGTH: 21
<212> TYPE: DNA
<213> ORGANISM: Triticum sp.

<400> SEQUENCE: 399
atggagtggt cacactttga a                                           21

<210> SEQ ID NO 400
<211> LENGTH: 22
<212> TYPE: DNA
<213> ORGANISM: Triticum sp.

<400> SEQUENCE: 400
agcttctctg accaacttct cg                                          22

<210> SEQ ID NO 401
<211> LENGTH: 21
<212> TYPE: DNA
<213> ORGANISM: Triticum sp.

<400> SEQUENCE: 401
caactcagtg ctcacacaac g                                           21

<210> SEQ ID NO 402
<211> LENGTH: 21
<212> TYPE: DNA
<213> ORGANISM: Triticum sp.

<400> SEQUENCE: 402
cgataaccac tcatccacac c                                           21

<210> SEQ ID NO 403
<211> LENGTH: 17
<212> TYPE: DNA
<213> ORGANISM: Triticum sp.

<400> SEQUENCE: 403
cggccctatc atggctg                                                17

<210> SEQ ID NO 404
<211> LENGTH: 20
<212> TYPE: DNA
<213> ORGANISM: Triticum sp.

<400> SEQUENCE: 404
gcttgcaagt tccattttgc                                             20
```

```
<210> SEQ ID NO 405
<211> LENGTH: 20
<212> TYPE: DNA
<213> ORGANISM: Triticum sp.

<400> SEQUENCE: 405
tcatacgggt atggttggac                                                  20

<210> SEQ ID NO 406
<211> LENGTH: 18
<212> TYPE: DNA
<213> ORGANISM: Triticum sp.

<400> SEQUENCE: 406
cacccccttg ttggtcac                                                    18

<210> SEQ ID NO 407
<211> LENGTH: 22
<212> TYPE: DNA
<213> ORGANISM: Triticum sp.

<400> SEQUENCE: 407
atgggttcgt actaacatca gc                                               22

<210> SEQ ID NO 408
<211> LENGTH: 20
<212> TYPE: DNA
<213> ORGANISM: Triticum sp.

<400> SEQUENCE: 408
ttgctggtag cttcaatccc                                                  20

<210> SEQ ID NO 409
<211> LENGTH: 22
<212> TYPE: DNA
<213> ORGANISM: Triticum sp.

<400> SEQUENCE: 409
tgctgctact tgtacagagg ac                                               22

<210> SEQ ID NO 410
<211> LENGTH: 18
<212> TYPE: DNA
<213> ORGANISM: Triticum sp.

<400> SEQUENCE: 410
ccgaattgtc cgccatag                                                    18

<210> SEQ ID NO 411
<211> LENGTH: 20
<212> TYPE: DNA
<213> ORGANISM: Triticum sp.

<400> SEQUENCE: 411
acatcgctct tcacaaaccc                                                  20

<210> SEQ ID NO 412
<211> LENGTH: 19
<212> TYPE: DNA
<213> ORGANISM: Triticum sp.

<400> SEQUENCE: 412
agttccggtc atggctagg                                                   19
```

```
<210> SEQ ID NO 413
<211> LENGTH: 22
<212> TYPE: DNA
<213> ORGANISM: Triticum sp.

<400> SEQUENCE: 413
attgaacagg aagacatcag gg                                              22

<210> SEQ ID NO 414
<211> LENGTH: 18
<212> TYPE: DNA
<213> ORGANISM: Triticum sp.

<400> SEQUENCE: 414
ttcctggagc tgtctggc                                                   18

<210> SEQ ID NO 415
<211> LENGTH: 21
<212> TYPE: DNA
<213> ORGANISM: Triticum sp.

<400> SEQUENCE: 415
gagagcctcg cgaaatatag g                                               21

<210> SEQ ID NO 416
<211> LENGTH: 19
<212> TYPE: DNA
<213> ORGANISM: Triticum sp.

<400> SEQUENCE: 416
tgcttctggt gttccttcg                                                  19

<210> SEQ ID NO 417
<211> LENGTH: 20
<212> TYPE: DNA
<213> ORGANISM: Triticum sp.

<400> SEQUENCE: 417
gtagtgaaga caagggcatt                                                 20

<210> SEQ ID NO 418
<211> LENGTH: 20
<212> TYPE: DNA
<213> ORGANISM: Triticum sp.

<400> SEQUENCE: 418
ccgaaagttg ggtgatatac                                                 20

<210> SEQ ID NO 419
<211> LENGTH: 22
<212> TYPE: DNA
<213> ORGANISM: Triticum sp.

<400> SEQUENCE: 419
acttgtatgc tccattgatt gg                                              22

<210> SEQ ID NO 420
<211> LENGTH: 20
<212> TYPE: DNA
<213> ORGANISM: Triticum sp.

<400> SEQUENCE: 420
```

```
ggggagtgga aactgcataa                                          20
```

<210> SEQ ID NO 421
<211> LENGTH: 20
<212> TYPE: DNA
<213> ORGANISM: Triticum sp.

<400> SEQUENCE: 421

```
ggctatctct ggcgctaaaa                                          20
```

<210> SEQ ID NO 422
<211> LENGTH: 19
<212> TYPE: DNA
<213> ORGANISM: Triticum sp.

<400> SEQUENCE: 422

```
tccacaaaca agtagcgcc                                           19
```

<210> SEQ ID NO 423
<211> LENGTH: 20
<212> TYPE: DNA
<213> ORGANISM: Triticum sp.

<400> SEQUENCE: 423

```
agccaccatc agcaaaaatt                                          20
```

<210> SEQ ID NO 424
<211> LENGTH: 20
<212> TYPE: DNA
<213> ORGANISM: Triticum sp.

<400> SEQUENCE: 424

```
gaacatgagc agtttggcac                                          20
```

<210> SEQ ID NO 425
<211> LENGTH: 21
<212> TYPE: DNA
<213> ORGANISM: Triticum sp.

<400> SEQUENCE: 425

```
atccgtagca cctactggtc a                                        21
```

<210> SEQ ID NO 426
<211> LENGTH: 20
<212> TYPE: DNA
<213> ORGANISM: Triticum sp.

<400> SEQUENCE: 426

```
ggtctgttca tgccacattg                                          20
```

<210> SEQ ID NO 427
<211> LENGTH: 20
<212> TYPE: DNA
<213> ORGANISM: Triticum sp.

<400> SEQUENCE: 427

```
aacacaatgg caaatgcaga                                          20
```

<210> SEQ ID NO 428
<211> LENGTH: 22
<212> TYPE: DNA
<213> ORGANISM: Triticum sp.

<400> SEQUENCE: 428
ccttcctagt aagtgtgcct ca                                              22

<210> SEQ ID NO 429
<211> LENGTH: 20
<212> TYPE: DNA
<213> ORGANISM: Triticum sp.

<400> SEQUENCE: 429
aatcacaaca aggcgtgaca                                                 20

<210> SEQ ID NO 430
<211> LENGTH: 17
<212> TYPE: DNA
<213> ORGANISM: Triticum sp.

<400> SEQUENCE: 430
cagggtggtg catgcat                                                    17

<210> SEQ ID NO 431
<211> LENGTH: 19
<212> TYPE: DNA
<213> ORGANISM: Triticum sp.

<400> SEQUENCE: 431
aaataggaca acccacggc                                                  19

<210> SEQ ID NO 432
<211> LENGTH: 20
<212> TYPE: DNA
<213> ORGANISM: Triticum sp.

<400> SEQUENCE: 432
tcaacttctt ggcctccatc                                                 20

<210> SEQ ID NO 433
<211> LENGTH: 20
<212> TYPE: DNA
<213> ORGANISM: Triticum sp.

<400> SEQUENCE: 433
actgcgtgtg cctacaattg                                                 20

<210> SEQ ID NO 434
<211> LENGTH: 19
<212> TYPE: DNA
<213> ORGANISM: Triticum sp.

<400> SEQUENCE: 434
tcactcgcac tcgataggc                                                  19

<210> SEQ ID NO 435
<211> LENGTH: 20
<212> TYPE: DNA
<213> ORGANISM: Triticum sp.

<400> SEQUENCE: 435
aaggcgaatc aaacggaata                                                 20

<210> SEQ ID NO 436
<211> LENGTH: 20
<212> TYPE: DNA
<213> ORGANISM: Triticum sp.

```
<400> SEQUENCE: 436
gttgctttag gggaaaagcc                                              20

<210> SEQ ID NO 437
<211> LENGTH: 21
<212> TYPE: DNA
<213> ORGANISM: Triticum sp.

<400> SEQUENCE: 437
acataatgct tcctgtgcac c                                            21

<210> SEQ ID NO 438
<211> LENGTH: 20
<212> TYPE: DNA
<213> ORGANISM: Triticum sp.

<400> SEQUENCE: 438 gccactttg tgtcgttcct                                               20

<210> SEQ ID NO 439
<211> LENGTH: 17
<212> TYPE: DNA
<213> ORGANISM: Triticum sp.

<400> SEQUENCE: 439
gcatttcggg tgaaccc                                                 17

<210> SEQ ID NO 440
<211> LENGTH: 22
<212> TYPE: DNA
<213> ORGANISM: Triticum sp.

<400> SEQUENCE: 440
gttgcatgta tacgttaagc gg                                           22

<210> SEQ ID NO 441
<211> LENGTH: 22
<212> TYPE: DNA
<213> ORGANISM: Triticum sp.

<400> SEQUENCE: 441
tctcgctgtg aaatcctatt tc                                           22

<210> SEQ ID NO 442
<211> LENGTH: 18
<212> TYPE: DNA
<213> ORGANISM: Triticum sp.

<400> SEQUENCE: 442
aggcatggat agaggggc                                                18

<210> SEQ ID NO 443
<211> LENGTH: 22
<212> TYPE: DNA
<213> ORGANISM: Triticum sp.

<400> SEQUENCE: 443
tagaattctt tatggggtct gc                                           22

<210> SEQ ID NO 444
<211> LENGTH: 22
<212> TYPE: DNA
<213> ORGANISM: Triticum sp.
```

```
<400> SEQUENCE: 444
aggattccaa tccttcaaaa tt                                        22

<210> SEQ ID NO 445
<211> LENGTH: 20
<212> TYPE: DNA
<213> ORGANISM: Triticum sp.

<400> SEQUENCE: 445
cccacaagaa cctttgaaga                                           20

<210> SEQ ID NO 446
<211> LENGTH: 19
<212> TYPE: DNA
<213> ORGANISM: Triticum sp.

<400> SEQUENCE: 446
cattgtgtgt gcaaggcac                                            19

<210> SEQ ID NO 447
<211> LENGTH: 18
<212> TYPE: DNA
<213> ORGANISM: Triticum sp.

<400> SEQUENCE: 447
tgcccacaac ggaacttg                                             18

<210> SEQ ID NO 448
<211> LENGTH: 20
<212> TYPE: DNA
<213> ORGANISM: Triticum sp.

<400> SEQUENCE: 448
gcaaccacca agcacaaagt                                           20

<210> SEQ ID NO 449
<211> LENGTH: 22
<212> TYPE: DNA
<213> ORGANISM: Triticum sp.

<400> SEQUENCE: 449
gcgtcagata tgcctaccta gg                                        22

<210> SEQ ID NO 450
<211> LENGTH: 20
<212> TYPE: DNA
<213> ORGANISM: Triticum sp.

<400> SEQUENCE: 450
agtgagttag ccctgagcca                                           20

<210> SEQ ID NO 451
<211> LENGTH: 21
<212> TYPE: DNA
<213> ORGANISM: Triticum sp.

<400> SEQUENCE: 451
tctgtctacc catgggattt g                                         21

<210> SEQ ID NO 452
<211> LENGTH: 20
<212> TYPE: DNA
```

```
<213> ORGANISM: Triticum sp.

<400> SEQUENCE: 452
ctggcttcga ggtaagcaac                                         20

<210> SEQ ID NO 453
<211> LENGTH: 20
<212> TYPE: DNA
<213> ORGANISM: Triticum sp.

<400> SEQUENCE: 453
ggaaacttat tgattgaaat                                         20

<210> SEQ ID NO 454
<211> LENGTH: 20
<212> TYPE: DNA
<213> ORGANISM: Triticum sp.

<400> SEQUENCE: 454
tcaattttga cagaagaatt                                         20

<210> SEQ ID NO 455
<211> LENGTH: 18
<212> TYPE: DNA
<213> ORGANISM: Triticum sp.

<400> SEQUENCE: 455 tcgccttta cagtcggc                                            18

<210> SEQ ID NO 456
<211> LENGTH: 20
<212> TYPE: DNA
<213> ORGANISM: Triticum sp.

<400> SEQUENCE: 456
atgggtagct gagagccaaa                                         20

<210> SEQ ID NO 457
<211> LENGTH: 20
<212> TYPE: DNA
<213> ORGANISM: Triticum sp.

<400> SEQUENCE: 457
aagagataac atgcaagaaa                                         20

<210> SEQ ID NO 458
<211> LENGTH: 20
<212> TYPE: DNA
<213> ORGANISM: Triticum sp.

<400> SEQUENCE: 458
ttcaaatatg tgggaactac                                         20

<210> SEQ ID NO 459
<211> LENGTH: 22
<212> TYPE: DNA
<213> ORGANISM: Triticum sp.

<400> SEQUENCE: 459
atggcataat ttggtgaaat tg                                      22

<210> SEQ ID NO 460
<211> LENGTH: 22
```

```
<212> TYPE: DNA
<213> ORGANISM: Triticum sp.

<400> SEQUENCE: 460
tgtttcaagc ccaacttcta tt                                              22

<210> SEQ ID NO 461
<211> LENGTH: 20
<212> TYPE: DNA
<213> ORGANISM: Triticum sp.

<400> SEQUENCE: 461
aagcactacg aaaatatgac                                                 20

<210> SEQ ID NO 462
<211> LENGTH: 20
<212> TYPE: DNA
<213> ORGANISM: Triticum sp.

<400> SEQUENCE: 462
tcttaagggg tgttatcata                                                 20

<210> SEQ ID NO 463
<211> LENGTH: 20
<212> TYPE: DNA
<213> ORGANISM: Triticum sp.

<400> SEQUENCE: 463
ttcacaccca accaatagca                                                 20

<210> SEQ ID NO 464
<211> LENGTH: 20
<212> TYPE: DNA
<213> ORGANISM: Triticum sp.

<400> SEQUENCE: 464
tctaggcaga cacatgcctg                                                 20

<210> SEQ ID NO 465
<211> LENGTH: 19
<212> TYPE: DNA
<213> ORGANISM: Triticum sp.

<400> SEQUENCE: 465
gatccccaat tgcatgttg                                                  19

<210> SEQ ID NO 466
<211> LENGTH: 18
<212> TYPE: DNA
<213> ORGANISM: Triticum sp.

<400> SEQUENCE: 466
cttgcaactg ggggacac                                                   18
```